(12) United States Patent
Farr

(10) Patent No.: US 8,556,806 B2
(45) Date of Patent: Oct. 15, 2013

(54) WAVELENGTH MULTIPLEXING ENDOSCOPE

(75) Inventor: Mina Farr, Palo Alto, CA (US)

(73) Assignee: Vivid Medical, Inc., Palo Alto, CA (US)

( * ) Notice: Subject to any disclaimer, the term of this patent is extended or adjusted under 35 U.S.C. 154(b) by 1092 days.

(21) Appl. No.: 12/535,439

(22) Filed: Aug. 4, 2009

(65) Prior Publication Data

US 2009/0292168 A1 Nov. 26, 2009

Related U.S. Application Data

(63) Continuation-in-part of application No. 12/111,107, filed on Apr. 28, 2008, which is a continuation-in-part of application No. 11/233,684, filed on Sep. 23, 2005, now Pat. No. 8,480,566.

(60) Provisional application No. 60/612,889, filed on Sep. 24, 2004, provisional application No. 61/086,095, filed on Aug. 4, 2008.

(51) Int. Cl.
*A61B 1/06* (2006.01)
*A61B 1/04* (2006.01)

(52) U.S. Cl.
USPC .............................. 600/160; 600/109; 600/178

(58) Field of Classification Search
USPC .............................. 600/106, 109, 178, 179, 182
See application file for complete search history.

(56) References Cited

U.S. PATENT DOCUMENTS

| | | | | |
|---|---|---|---|---|
| 5,538,497 A * | 7/1996 | Hori | .............................. | 600/182 |
| 5,749,830 A * | 5/1998 | Kaneko et al. | ................. | 600/160 |
| 6,878,109 B2 * | 4/2005 | Yamaki et al. | ................. | 600/180 |
| 7,892,169 B2 * | 2/2011 | Gono et al. | ..................... | 600/178 |
| 8,212,858 B2 * | 7/2012 | Schechterman et al. | ......... | 348/42 |
| 2001/0007051 A1 * | 7/2001 | Nakashima | .................... | 600/179 |
| 2002/0120181 A1 * | 8/2002 | Irion | .............................. | 600/178 |
| 2003/0120130 A1 * | 6/2003 | Glukhovsky et al. | .......... | 600/109 |
| 2004/0039242 A1 * | 2/2004 | Tolkoff et al. | ..................... | 600/9 |
| 2004/0143162 A1 * | 7/2004 | Krattiger et al. | .............. | 600/175 |
| 2004/0196364 A1 * | 10/2004 | Takahashi | ........................ | 348/65 |
| 2005/0038321 A1 | 2/2005 | Fujita et al. | | |
| 2005/0040424 A1 * | 2/2005 | Erchak et al. | ................. | 257/100 |
| 2005/0043586 A1 * | 2/2005 | Suzushima | .................... | 600/160 |
| 2005/0234296 A1 * | 10/2005 | Saadat et al. | ................... | 600/129 |
| 2006/0287582 A1 * | 12/2006 | Toda | .............................. | 600/178 |
| 2007/0015964 A1 | 1/2007 | Eversull et al. | | |
| 2007/0073109 A1 * | 3/2007 | Irion | .............................. | 600/179 |
| 2008/0207996 A1 | 8/2008 | Tsai | | |
| 2010/0198009 A1 | 8/2010 | Farr et al. | | |

OTHER PUBLICATIONS

International Search Report dated Apr. 23, 2012 as received in application No. PCT/US2011/052039.
Written Opinion of the International Searching Authority dated Apr. 23, 2012 as received in application No. PCT/US2011/052039.

* cited by examiner

*Primary Examiner* — Philip R Smith
*Assistant Examiner* — William Chou
(74) *Attorney, Agent, or Firm* — Maschoff Brennan

(57) ABSTRACT

Various embodiments for providing solid state illumination in conjunction with wavelength multiplexing imaging schemes for mono and stereo endoscopy or borescopy are provided. In one embodiment, the current disclosure provides a device configured for insertion into a body cavity. The device can include a tubular portion having a proximal end and a distal end. The distal end of the tubular portion can be configured to be at least partially inserted into the body cavity. The device can also include a solid state electro-optic element located on the tubular portion. Furthermore, the device can include a power source electrically coupled to the solid state electro-optic element.

20 Claims, 30 Drawing Sheets

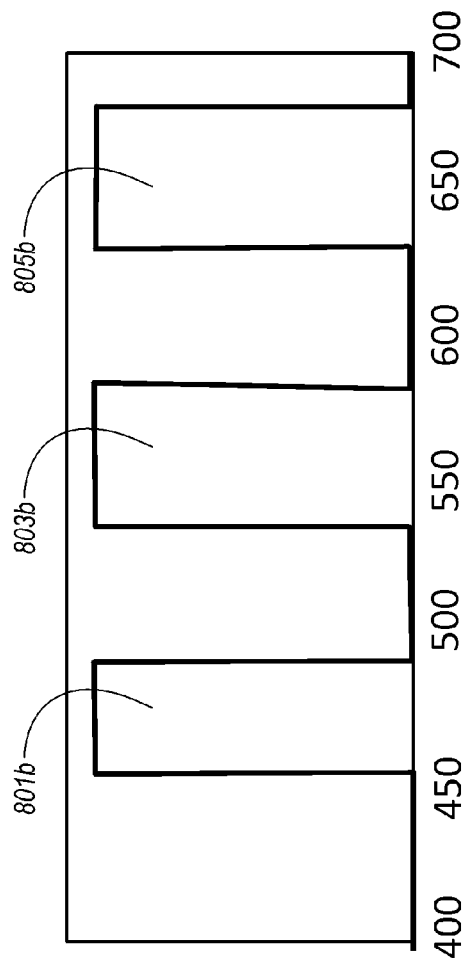
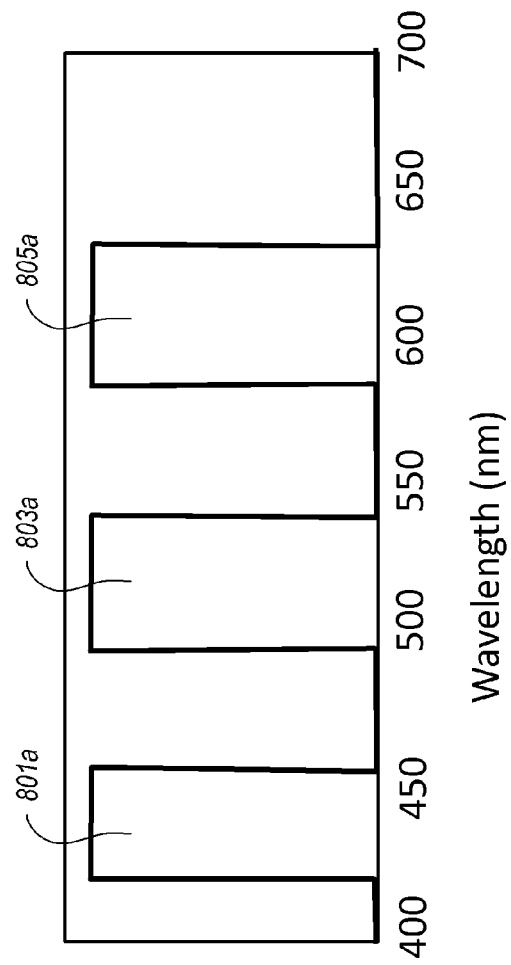
Fig. 9a
Fig. 9b

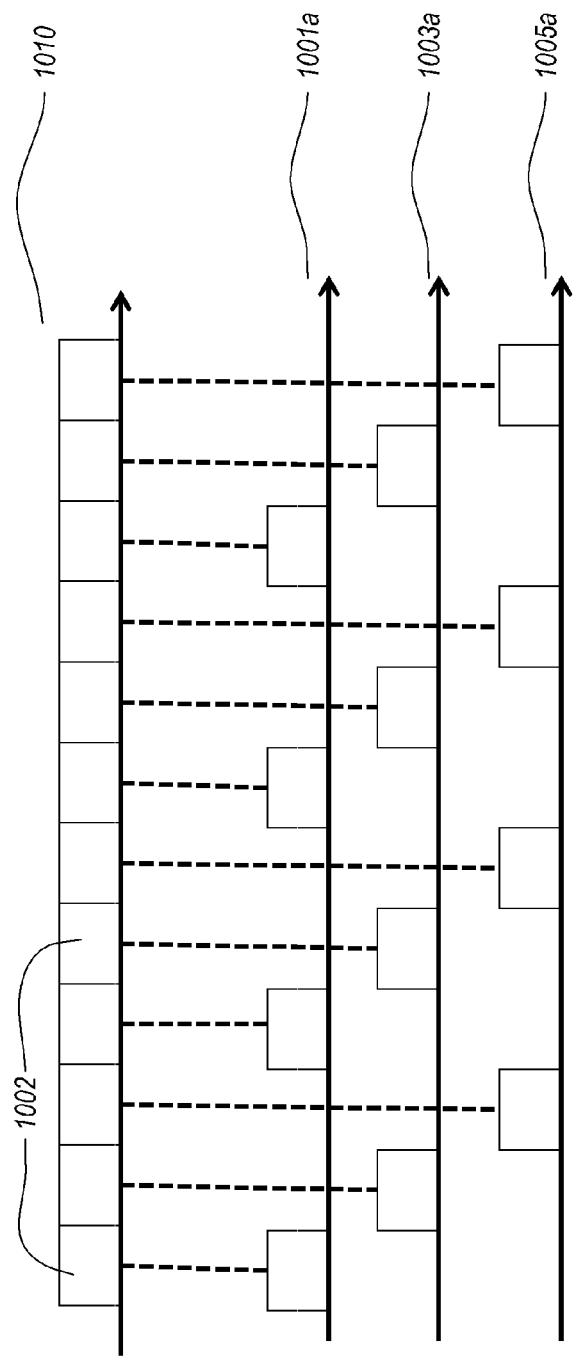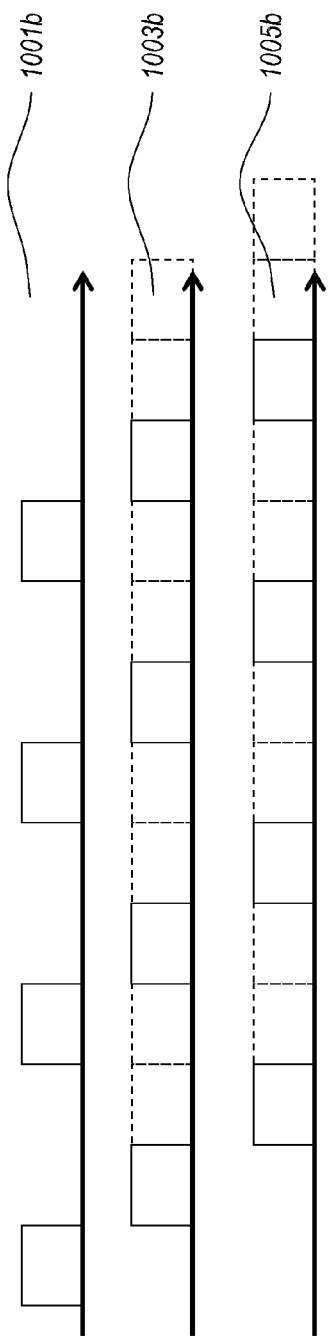

Wavelength (nm)

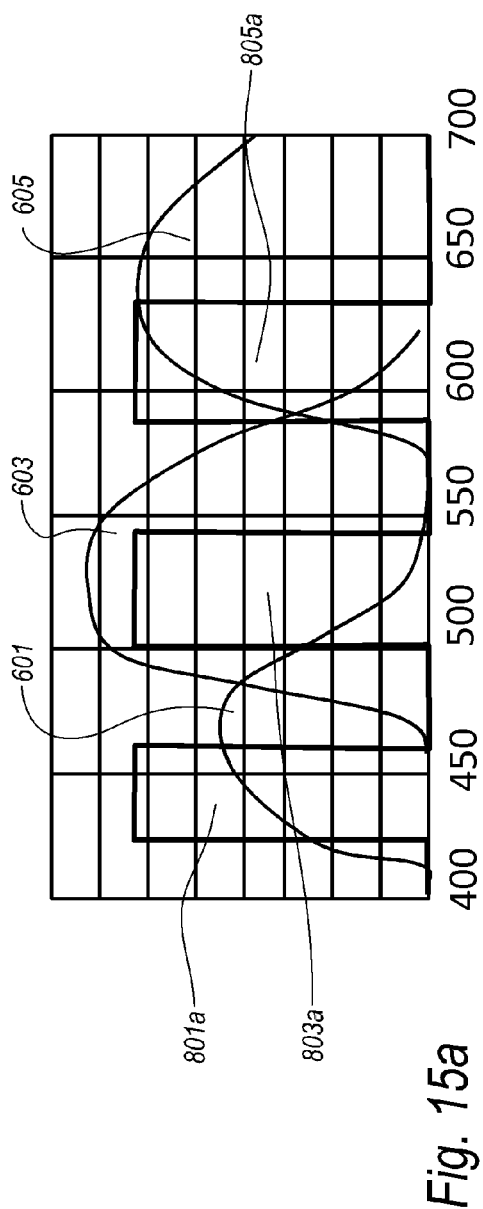
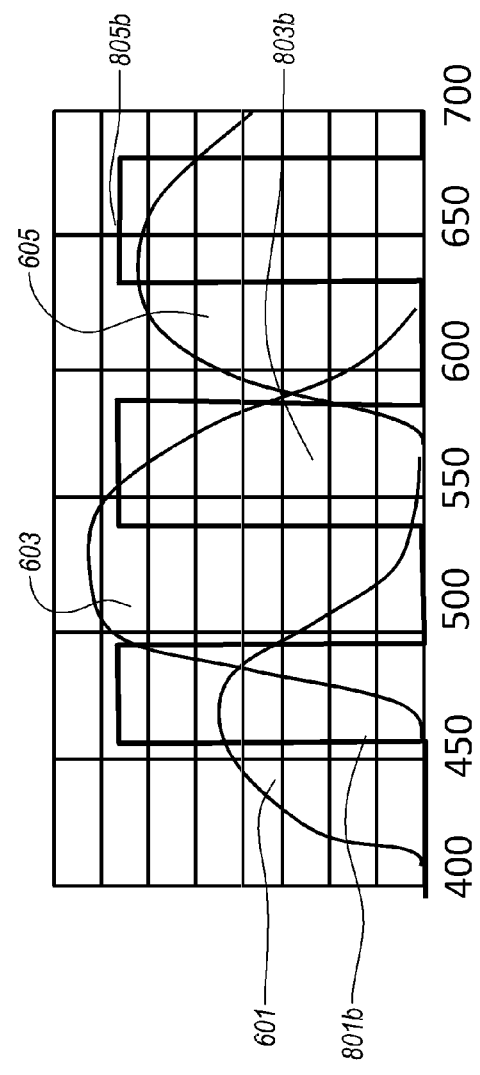
Fig. 15a
Fig. 15b

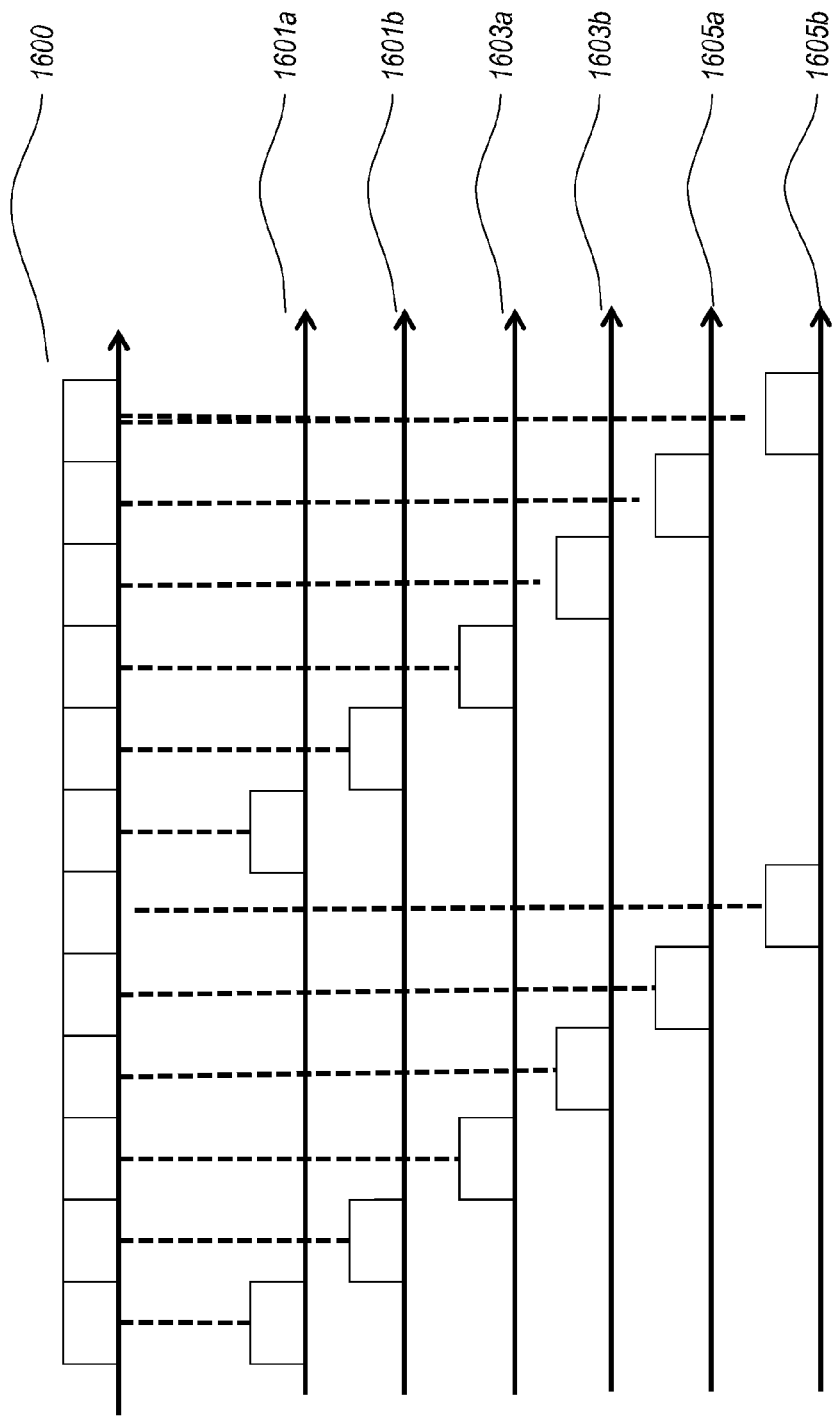

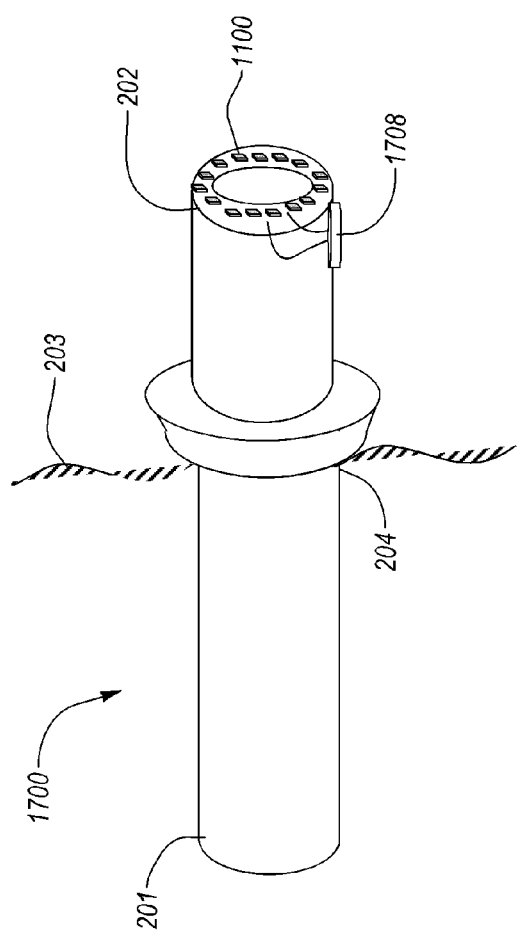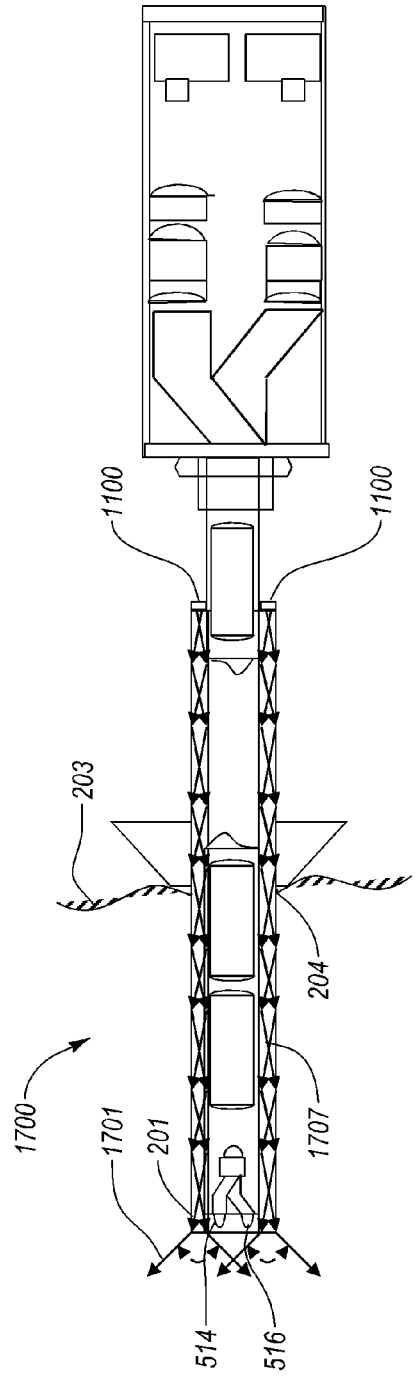

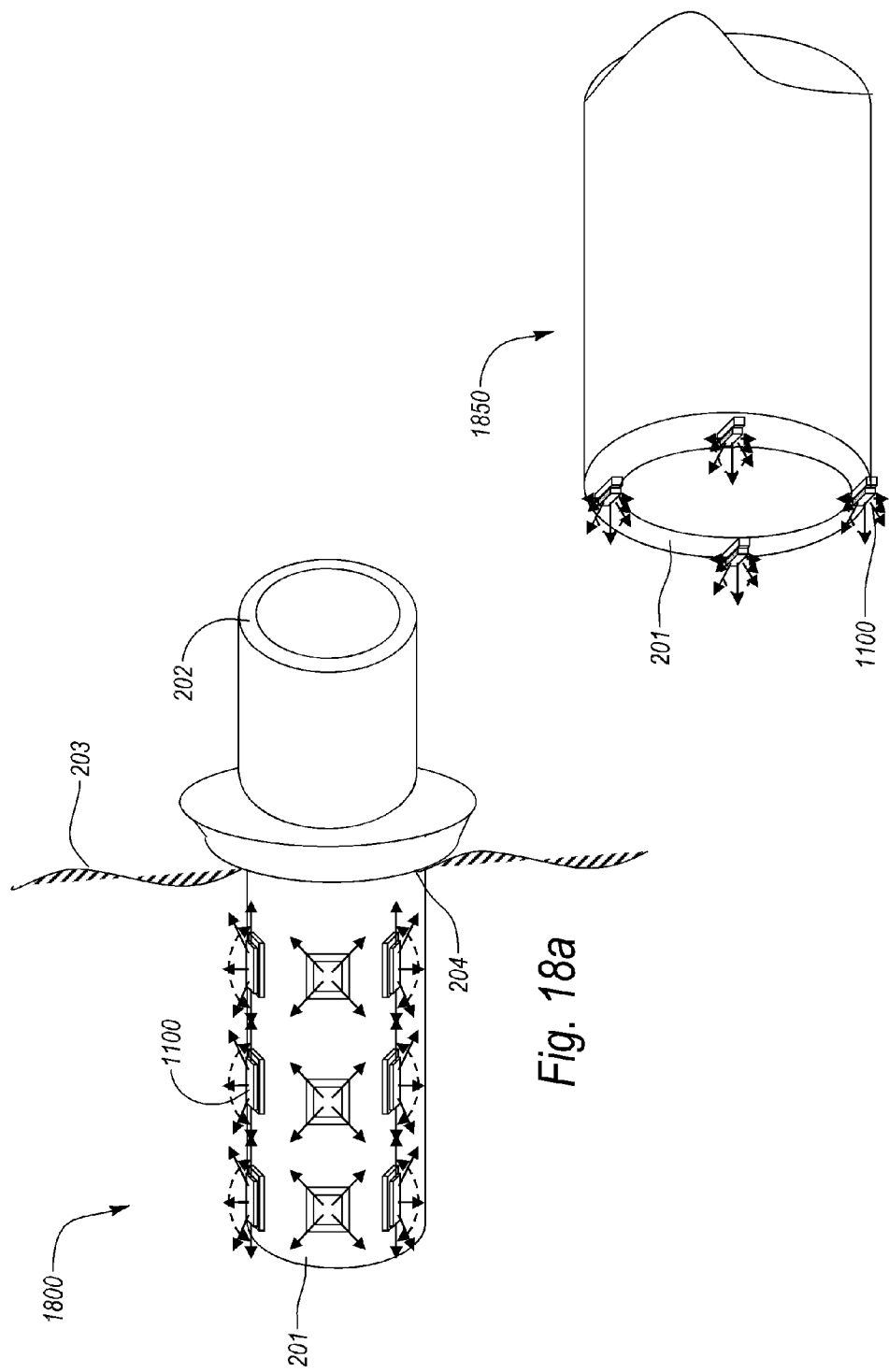

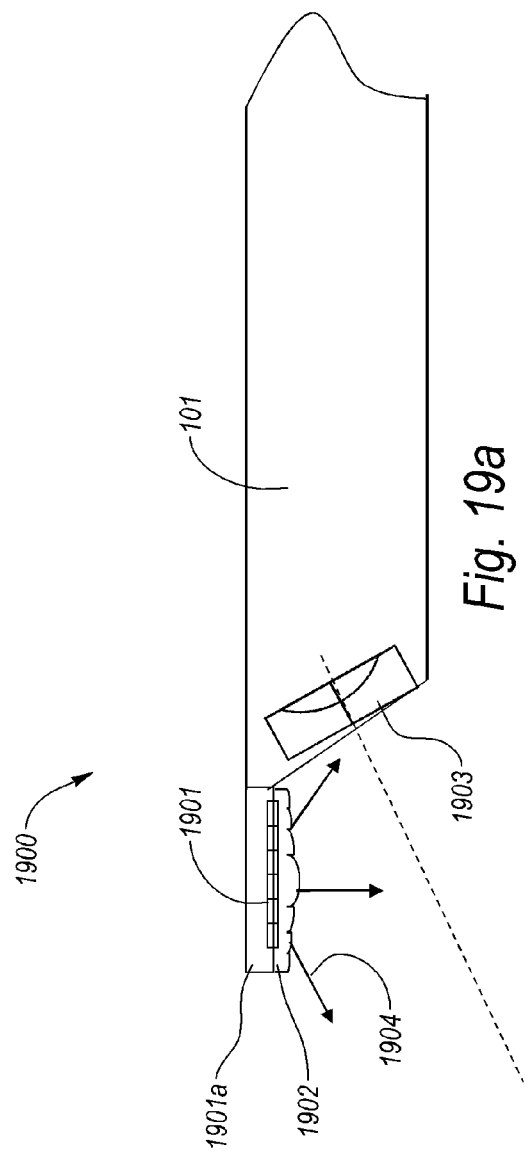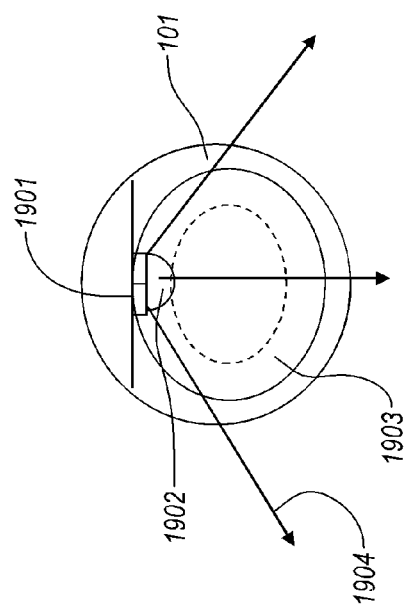

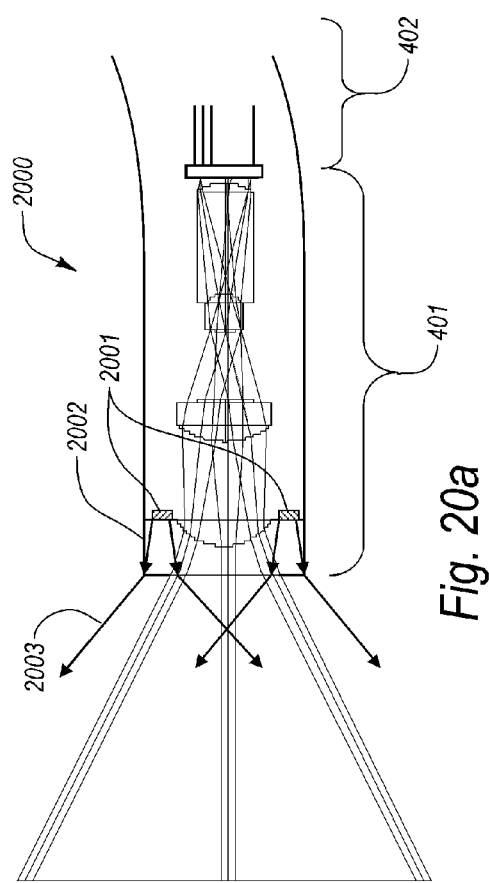
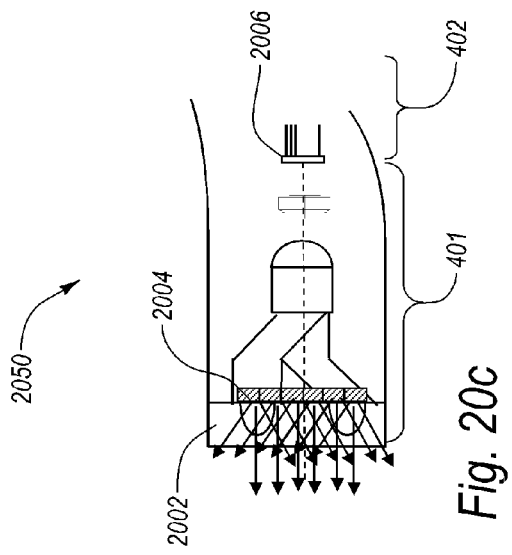
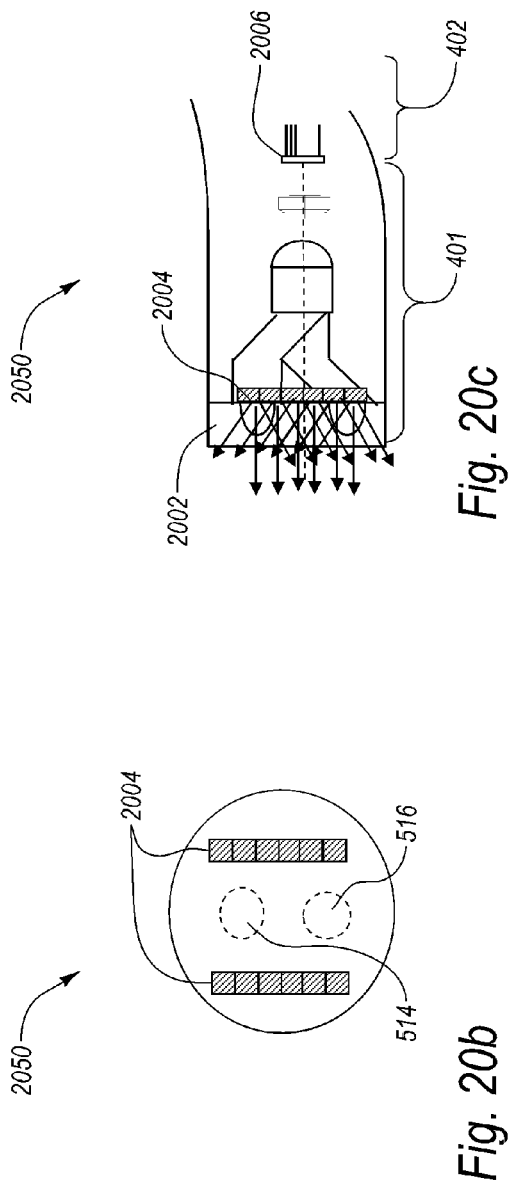

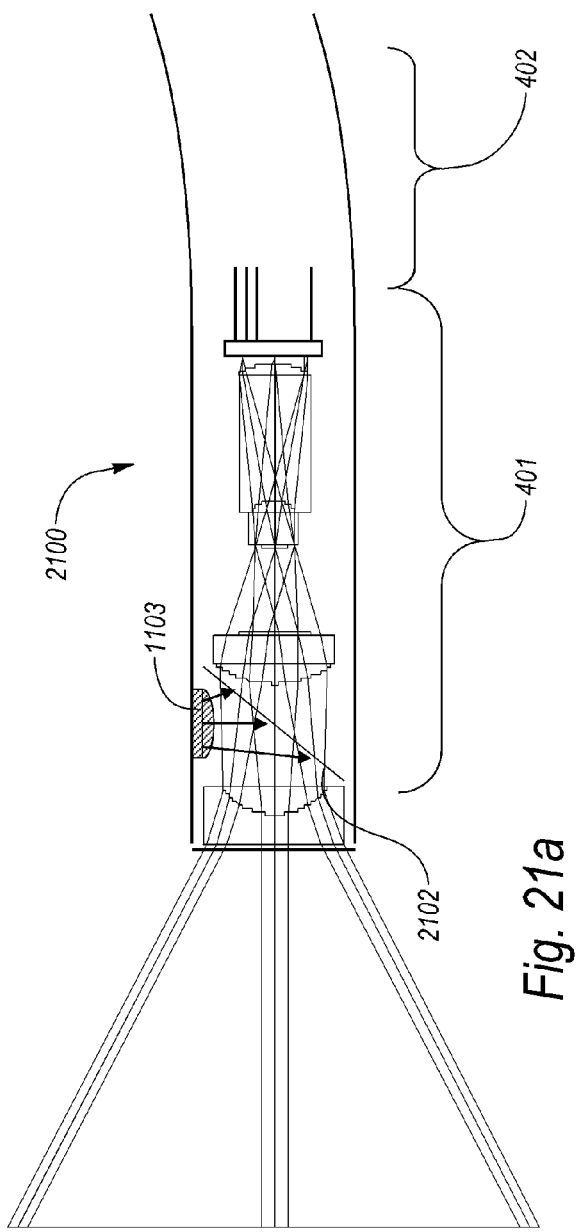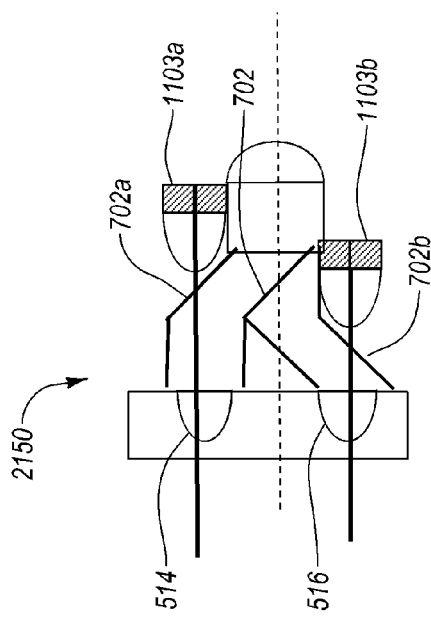
Fig. 21a
Fig. 21b

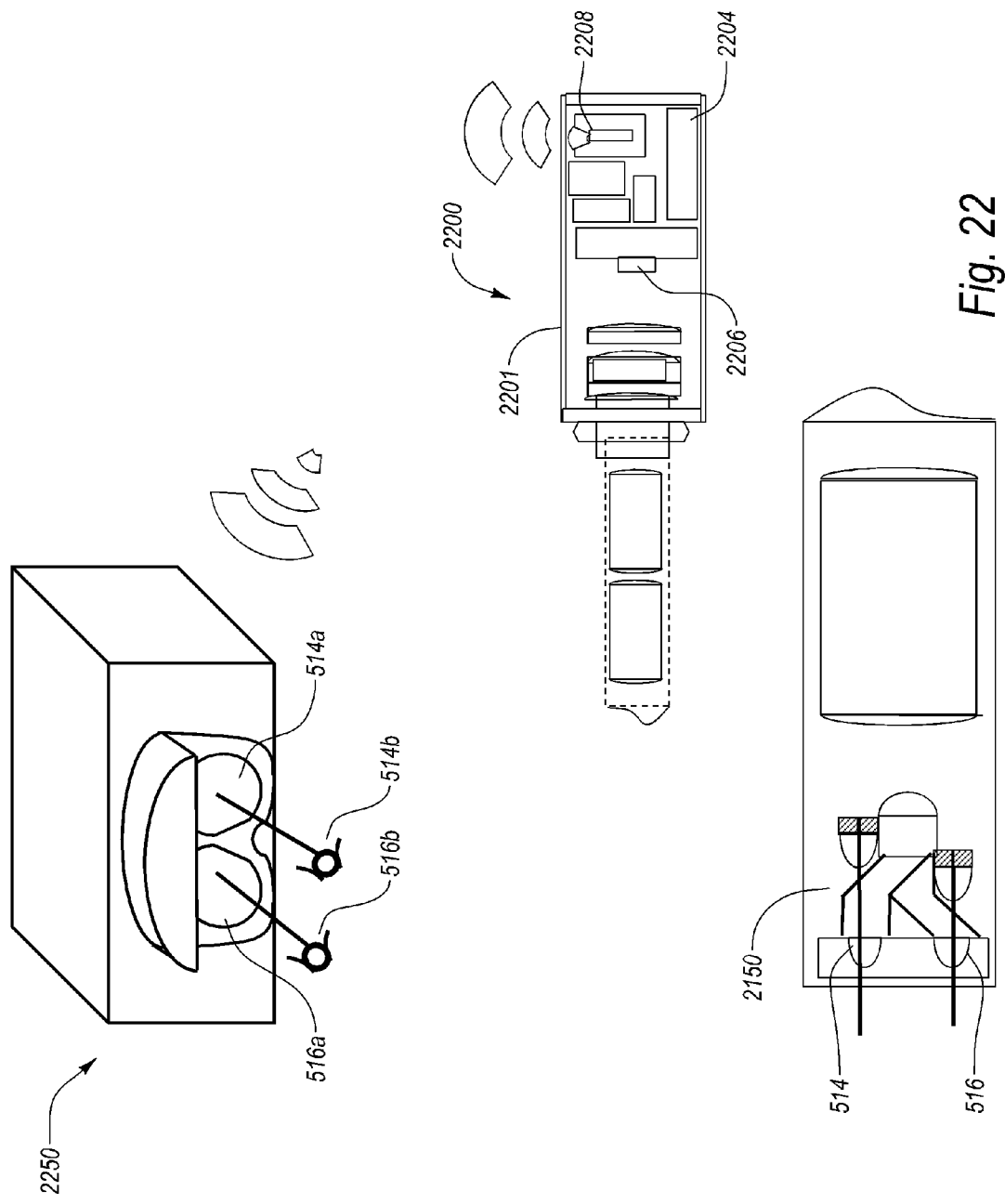

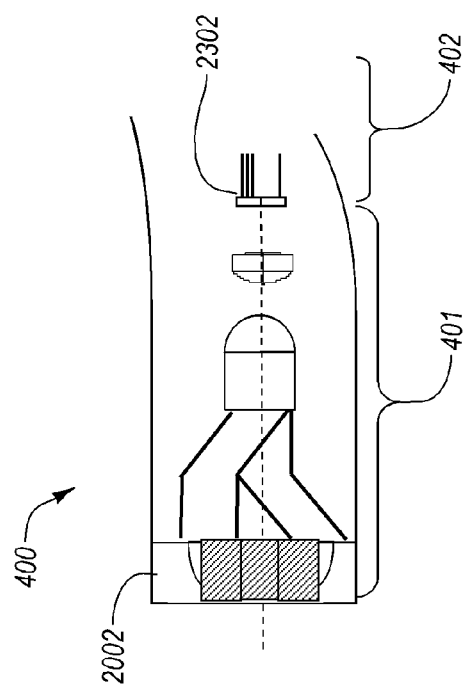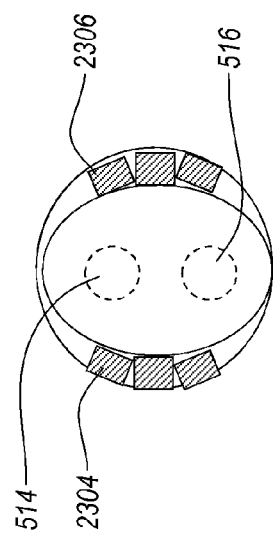
Fig. 23a
Fig. 23b

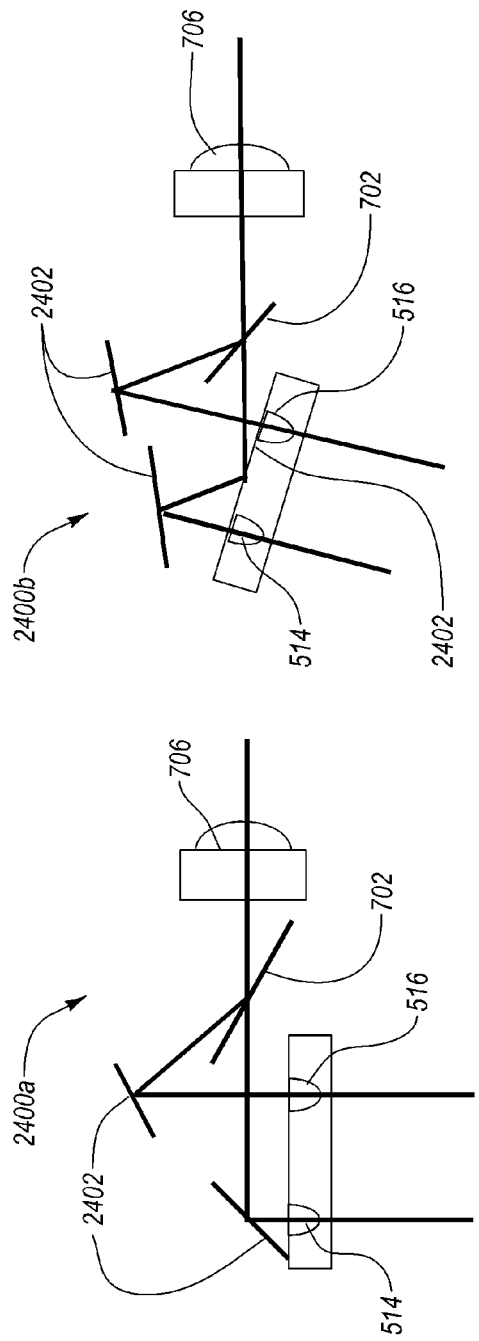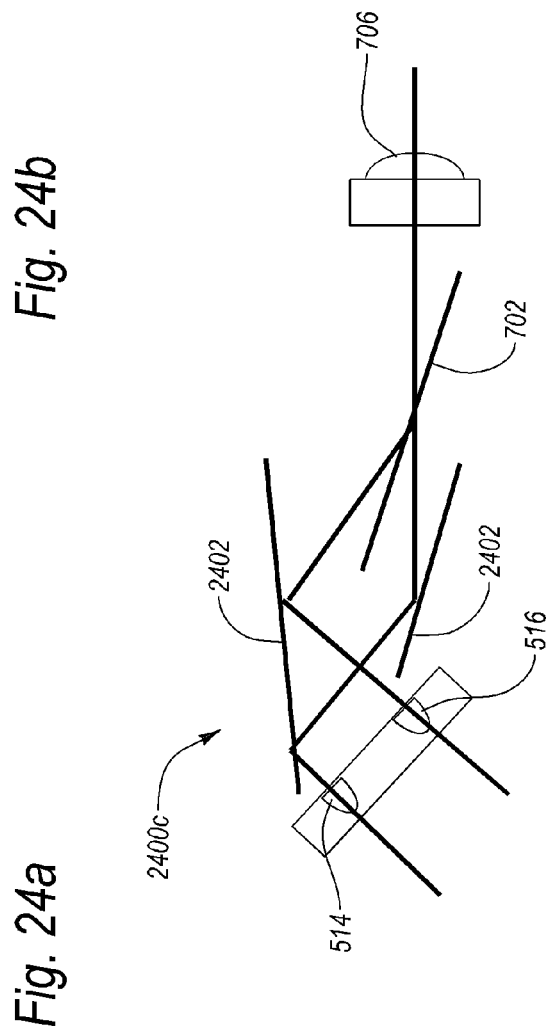
Fig. 24a
Fig. 24b
Fig. 24c

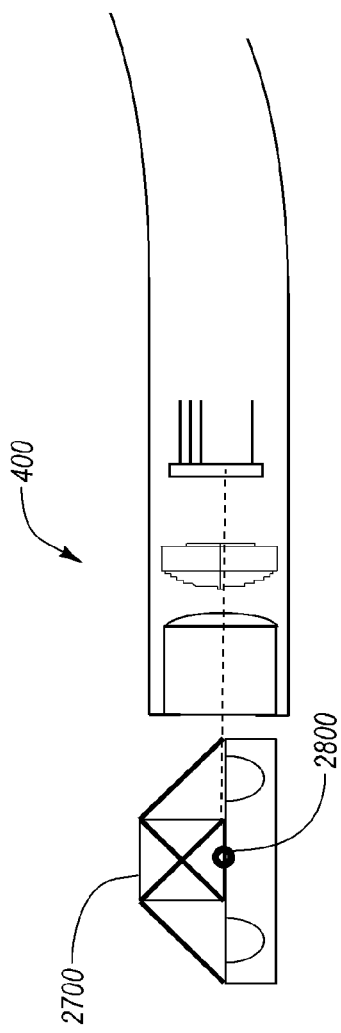
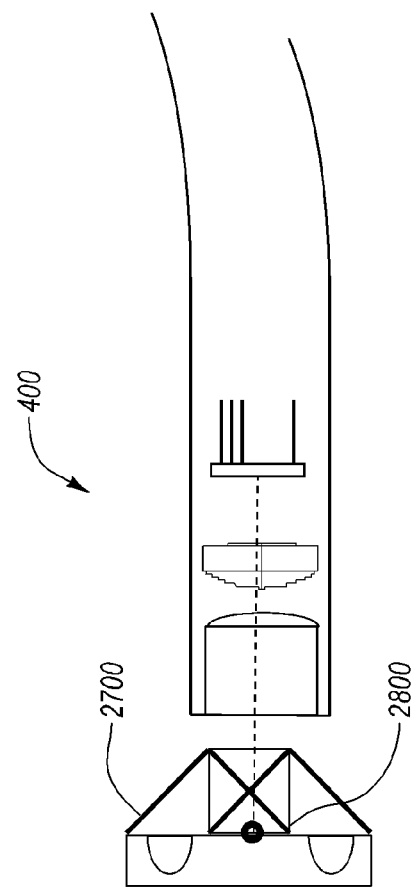
Fig. 29a
Fig. 29b

WAVELENGTH MULTIPLEXING ENDOSCOPE

CROSS-REFERENCE TO RELATED APPLICATIONS

This application is a continuation-in-part of U.S. patent application Ser. No. 12/111,107 filed Apr. 28, 2008, which is a continuation in part of U.S. patent application Ser. No. 11/233,684, filed Sep. 23, 2005, which claims the benefit of U.S. Provisional Patent Application Ser. No. 60/612,889 filed Sep. 24, 2004. This application also claims the benefit of and priority to U.S. Provisional Patent Application Ser. No. 61/086,095 filed Aug. 4, 2008. The foregoing patent applications are incorporated herein by reference in their entirety. This application also incorporates herein by reference U.S. patent application Ser. No. 12/502,942 filed Jul. 14, 2009 and U.S. Provisional Patent Application Ser. No. 61/082,432 filed Jul. 21, 2008 in their entirety.

BACKGROUND

1. Technical Field

The present disclosure relates generally to apparatus for the illumination of endoscopic and borescopic fields, in minimally invasive surgical (MIS) procedures, general or diagnostic medical or industrial procedures using stereo endoscopes or borescopes, respectively. More particularly, embodiments of the disclosure relate to use of a Light Emitting Photodiode and other solid state light sources in endoscopic and borescopic procedures, as a means of illumination for a single channel and single sensor method of stereoscopic imaging.

2. The Relevant Technology

Endoscopy is used in both diagnostic and surgical procedures. Currently, MIS procedures, as opposed to open surgical procedures, are routinely done in almost all hospitals. Minimally invasive surgical techniques minimize trauma to the patient by eliminating the need to make large incisions. This both reduces the risk of infection and reduces the patient's hospital stay. Laparoscopic and endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx/the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder, or vagina. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

Endoscopes can have a variety of forms, ranging in diameter, tube length, and angle of view. Endoscopes can be diagnostic, for observation only, or operative, having channels for irrigation, suction, and the insertion of accessory instruments when a surgical procedure is planned. Thus, endoscope bodies also could provide mechanical or electrical control sections, buttons for valves such as a suction valve, a CO2 valve, a water bottle connector, a water feed, a suction port, etc. The common component that all endoscopes must be equipped with is a light guide section for illumination.

Endoscopes commonly use optical fibers to illuminate the surgical site. Illumination is a very important part of laparoscopy because there is no light source inside the body. Fiber optic cold light is used to project light down the laparoscope from an external source. Large lamps with broadband output are used to couple light into the illumination light guides, where light guides transfer the illumination light from the light source to the illumination fiber bundle inside the endoscope body. One or more light guide bundles are used to couple light into the endoscope illumination fiber bundles.

The use of fiber bundles inside the endoscope body or tube occupies space that otherwise could have been used by the imaging optics, or used to reduce the diameter of the endoscope. In particular, the fiber optic illuminators share the endoscope body with the imaging optics. Limitations on the optical lens terrain diameter, as well as the imaging fiber bundle thickness, correlate directly to the imaging resolution vs. size of the image. The larger the lens diameter or imaging bundle thickness, the better the resolution of the endoscope for a certain field of view (FOV) or image size. This is the main reason that larger diameter scopes are considered better in optical quality than narrower scopes. However, large scope diameters are not desirable for certain operations where space is limited on the operation site.

The illumination fiber port(s) of an endoscope commonly join the endoscope body at some angle near the eyepiece at the proximal side of the endoscope. The fiber guide body and the main endoscope body are commonly joined together in a welding process at joint. The construction and design of this welded joint is often a weakness in the endoscope manufacturing and use, where after many operations, high temperature and high humidity sterilizations, and successive handling, this welded joint could get damaged and break, exposing the internal parts of the endoscope to the environment when the seal is broken.

Accordingly, a number of weaknesses and disadvantages exist with respect to conventional endoscopes and corresponding methods and systems.

BRIEF SUMMARY

These and other limitations are overcome by the embodiments of the current disclosure, which relate to wavelength multiplexing of illumination wavelengths in an endoscope, enabling a single channel and/or a single imaging sensor to be used to capture images from 2 or more optical ports at the distal end of the endoscope.

Time synchronized solid state illumination, or filtered light from a solid state light source can be used in conjunction with wavelength multiplexing optics to combine spectral imaging data through single relay or imaging optics onto one or more image sensors. Stereo vision is highly desirable in endoscopic and borescopic fields where depth perception increases confidence and reduces time of procedure. In various embodiment of current disclosure, a modified objective system is used in a single channel stereo endoscope, where wavelength multiplexed stereo video information can be captured by one or more regular red, green, blue ("RGB") or Black and White image sensors.

Using a single channel and single image sensor to achieve wide color gamut, with time synchronized illumination and multi-port wavelength multiplexed imaging, not only reduces the diameter of the endoscope and the size of the camera module, it also allows multi-chip image quality and multiport imaging such as stereo optics to be possible in a single sensor flexible endoscope. The embodiments of this disclosure provide detailed information on how a much simpler system can be used to achieve 3-chip quality color images in stereo without duplicating any of the imaging optics, sensor electronics, or use of special sensors.

A wireless embodiment of a 3-chip quality, stereo endoscope is also presented, where a single sensor can communicate with separate electronics and display systems, sending a single sensor image data instead of dual, three-chip camera signals to achieve stereo vision.

BRIEF DESCRIPTION OF THE DRAWINGS

To further clarify the above and features of the present disclosure, a more particular description will be rendered by reference to specific embodiments, which are illustrated in the appended drawings. It is appreciated that these drawings depict only example embodiments of the disclosure and are therefore not to be considered limiting of its scope. The disclosure will be described and explained with additional specificity and detail through the use of the accompanying drawings in which:

FIG. 9a and 9b illustrate the 3-band RGB dichroic mirror reflection and transmission spectra.

FIGS. 10a and 10b illustrate RGB illuminated endoscope video signal, where the RGB illumination is time synchronized with the video frame rate;

FIGS. 15a and 15b illustrate the two sets of shorter and longer RGB illumination separately sampling the entire RGB detection and display area.

FIG. 16a illustrates a 6 illuminator turn on cycles (2×RGB) frame synchronized with a single black and white image sensor;

FIGS. 17a and 17b illustrate a self lighted cannula, using multiple LED sources installed at the proximal end of the cannula, with a single channel stereo endoscope inserted in the cannula.

FIGS. 18a and 18b illustrate a cannula with built-in LED illuminators on the body and at the distal end of the cannula;

FIGS. 19a and 19b illustrate an angled endoscope with modified distal tip, incorporating an array of LEDs for illumination of the surgical site in a pluggable and removable fashion;

FIG. 20a-c illustrate fixed solid state illuminators assembled behind the first negative lens of the endoscope, used as a window at the distal end of a flexible endoscope;

FIGS. 21a and 21b illustrate inclusion of the LED sources within the objective lens assembly of an endoscope, using a beam splitter in a mono or stereo endoscope geometry;

FIG. 22 illustrates a wavelength multiplexed single channel, single sensor stereo endoscope communicating wirelessly to a controller and 3D viewer.

FIGS. 23a and 23b illustrate a wavelength multiplexed stereo tip for a flexible endoscope, with 2 sets of RGB LED illuminators mounted next to the imaging window;

FIG. 24a-c illustrate the wavelength multiplexed stereo objective assembly for various angled endoscope geometries;

FIGS. 29a and 29b illustrate a deployable wavelength multiplexed stereo objective incorporated at the distal tip of a flexible endoscope, before and after deployment inside the body.

DETAILED DESCRIPTION

Exemplary embodiments of the disclosure concern monochromatic or polychromatic solid state light sources such as high power Light Emitting Devices (LEDs) and Laser Diodes as a means of illumination in a diagnostic or surgical endoscopic procedures, or functional borescopic systems, and how these polychromatic light sources can be used to achieve wavelength multiplexed imaging in the endoscope. In particular, these solid state light sources are incorporated at the distal end of the endoscope, borescope, surgical or industrial tools, and the tip end of cannulas, catheters, and other functional devices. They can also be incorporated in an illumination body that is inserted separately, or in conjunction with a lighted or dark scope, into the body. The illumination of an object inside a body, a body herein being defined as at least a portion of a human, animal, or physical object not easily accessible, is performed to detect the modified light, image the object, or manipulate a change in the object.

Use of such solid state sources inside a cavity in the body, replaces a variety of instruments otherwise needed for the same purpose, such as an external light source, fiber light guides, and means of transmitting the light to the desired object.

For example, the use of LED sources has several advantages over the conventional external white light source. With an LED-based illumination, a true, visible light source with no IR content is available for the endoscopic application. Therefore, the complicated IR management of the light source is eliminated. There is no longer a fire hazard associated with light guides that may be left on, and no heat management inside the scope is needed.

LEDs can provide light at any region of the visible spectrum. Red, Green, and Blue LEDs in primary colors can be used together to form a white illumination, Phosphor-converted LEDs can provide white output directly without any color mixing, Infra Red (IR) or Ultraviolet (UV) LEDs can be used for their special characteristic in light transmission in the medium of insertion or the effect they have on the object of interest.

Figure 1:
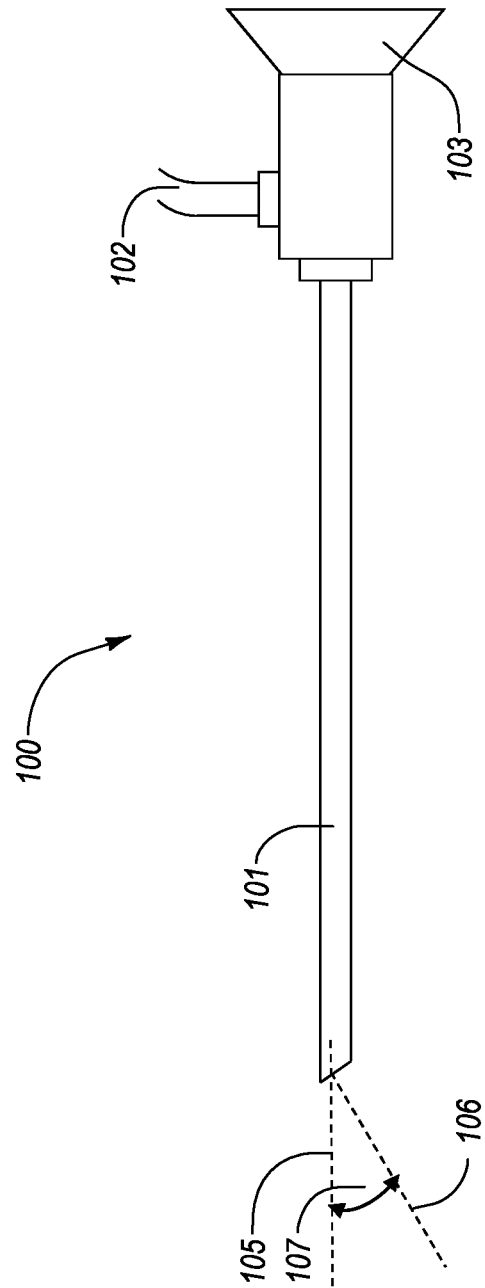
FIG. 1 illustrates a typical angled endoscope, with fiber optic light port for illumination, and an eye piece for viewing.

An example laparoscope or arthroscope is shown in FIG. 1 as a rigid endoscope. It allows for visualization of the abdominopelvic cavities, or orthopedic joint areas, respectively, for diagnostic or surgical techniques. The rigid endoscope is inserted into the peritoneal cavity via a cannula that runs through the abdominal or body wall. There are many different features of endoscopes, such as the size and field of vision, which determine the effectiveness of the instrument.

Figure 3:
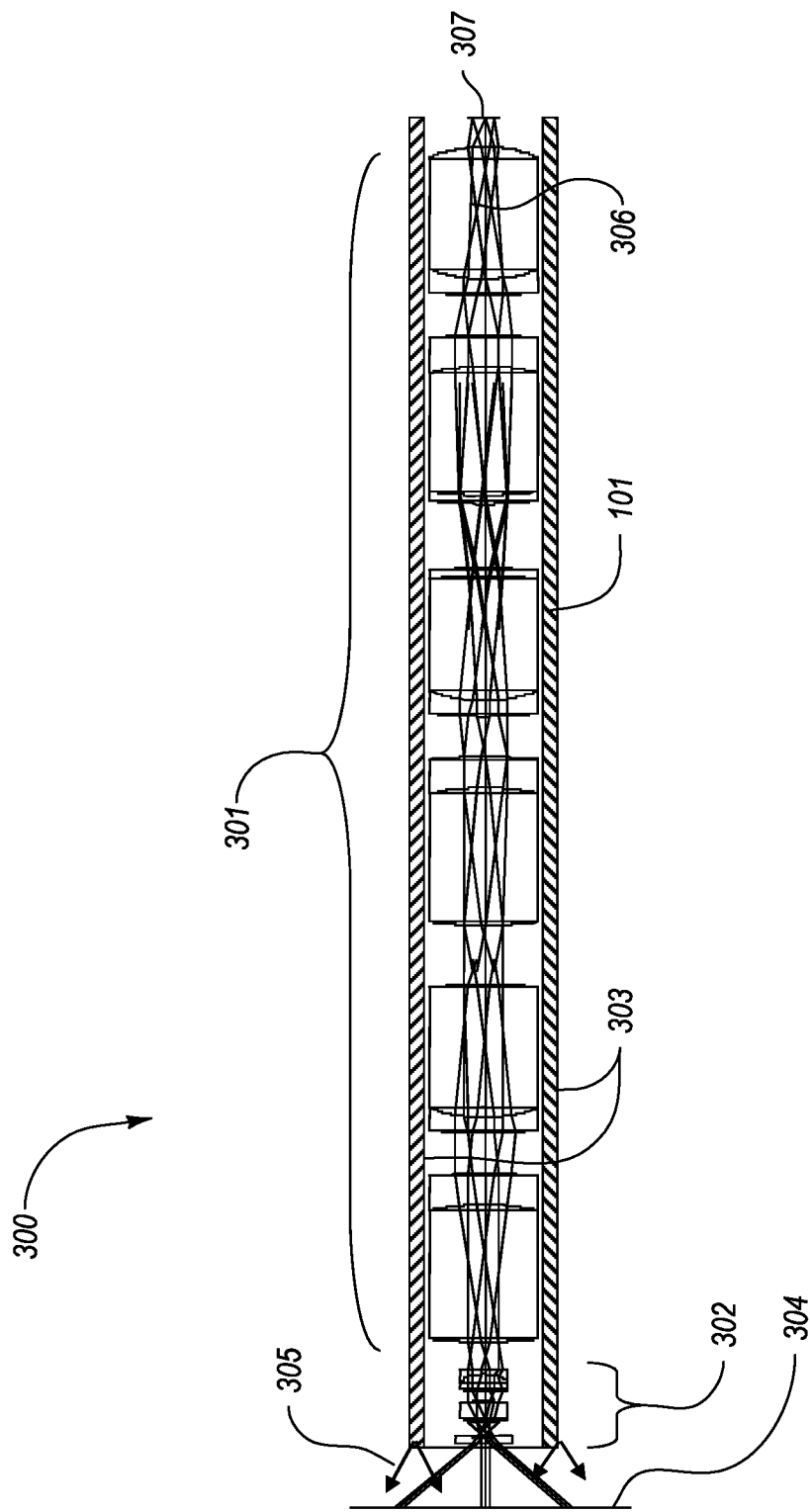
FIG. 3 illustrates the cross section of a typical zero degree, rigid endoscope with associated terrain for relay of the image through the length of the endoscope.

As illustrated in FIG. 1, the basic rigid endoscope is made up of a long thin tube forming the endoscope body 101 with an eyepiece 103 at one end for viewing into the patient. Fiber optic light introduced to the endoscope at a fiber port 102, and launched into fiber optics 303 (FIG. 3), passes through the endoscope body 101, illuminating the area 304 (FIG. 3) that is being observed, as illustrated by radiation pattern 305 (FIG. 3). Rigid Endoscopes are characterized by diameter and the direction of view. The direction of view (angle of endoscope) is the angle 107 between the axis of the endoscope 105 and the center field of view 106, as illustrated in FIG. 1. Typical endoscopes have lengths of approximately 30 cm and diameters in the range of 3 to 10 mm. Endoscopes consist of two important lenses, the ocular lens at the eyepiece and the objective lens assembly 302 at the distal end of the endoscope 300, as shown in FIG. 3. Other lens sets acting as relay lenses 301 in FIG. 3, are used in between the objective lens assembly 302 and the eye piece or the image capture device, such as a charge coupled device (CCD), camera or image position 307. Imaging rays 306 traverse the length of the scope through all the imaging optics.

The rigid endoscope can also come in different viewing angles: 120 degree or retrograde, for viewing backward; 90 degree and 70 degree for lateral viewing; 30 degree and 45 degree for forward oblique views; and 0 degree for forward viewing. The angle of the negative lens used in the objective lens assembly 302 is determined by the position of the structure to be viewed.

Figure 2:
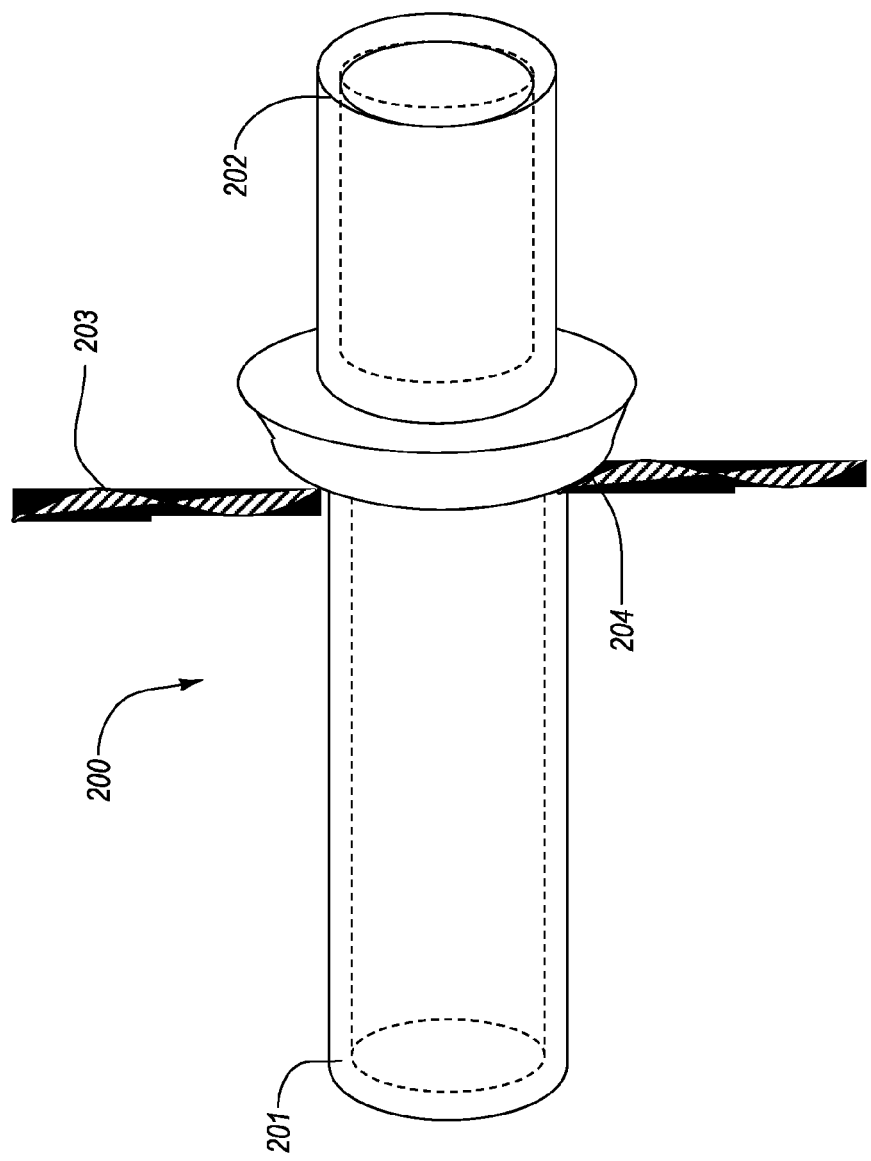
FIG. 2 illustrates a cannula inserted into the body cavity.

Other surgical instruments and tools are also inserted into the body, for the operation and specific surgical manipulation by the surgeon. The insertion is done through open tubes provided inside the endoscope body for instrument insertion, such as in gastrointestinal endoscopes, or through separate incisions in the abdominal, chest, or limb wall 203, using cannula 200, which are straight or curved stainless steel or plastic tubes which are inserted into a small opening or incision in the skin as illustrated in FIG. 2. The cannula opening at the proximal end 202 outside the body is used to guide different instruments inside the body, where they are exposed to the inside of body at the distal end 201 of the cannula 200. The cannula can also make a seal at the incision site 204.

In a typical gastrointestinal endoscope, a tool opening is provided at the distal end of the scope, where inserted medical instruments gain access to the body following the scope body. In endoscopic and surgical procedures through a natural orifice or vein, a flexible catheter body similar to cannula is used to gain access to a remote site inside the body.

An illustration showing typical endoscope optics is shown in FIG. 3. Common imaging sections of the endoscope 300 are an ocular or eyepiece 103 (FIG. 1), relay lenses (in the case of rigid scopes), a flexible imaging fiber-optic bundle (in the case of flexible scopes), and an objective lens assembly 302. Endoscopes are either used as stand alone units, with the surgeon looking into the scope from the ocular or eye piece of the endoscope, or in conjunction with digital cameras, where an image of the surgical site is incident on the image capture device (such as a complementary metal oxide semiconductor (CMOS) sensor or CCD) of the camera. Using a display device, the surgeon performs the operation looking at the image on the video monitor.

Figure 4:
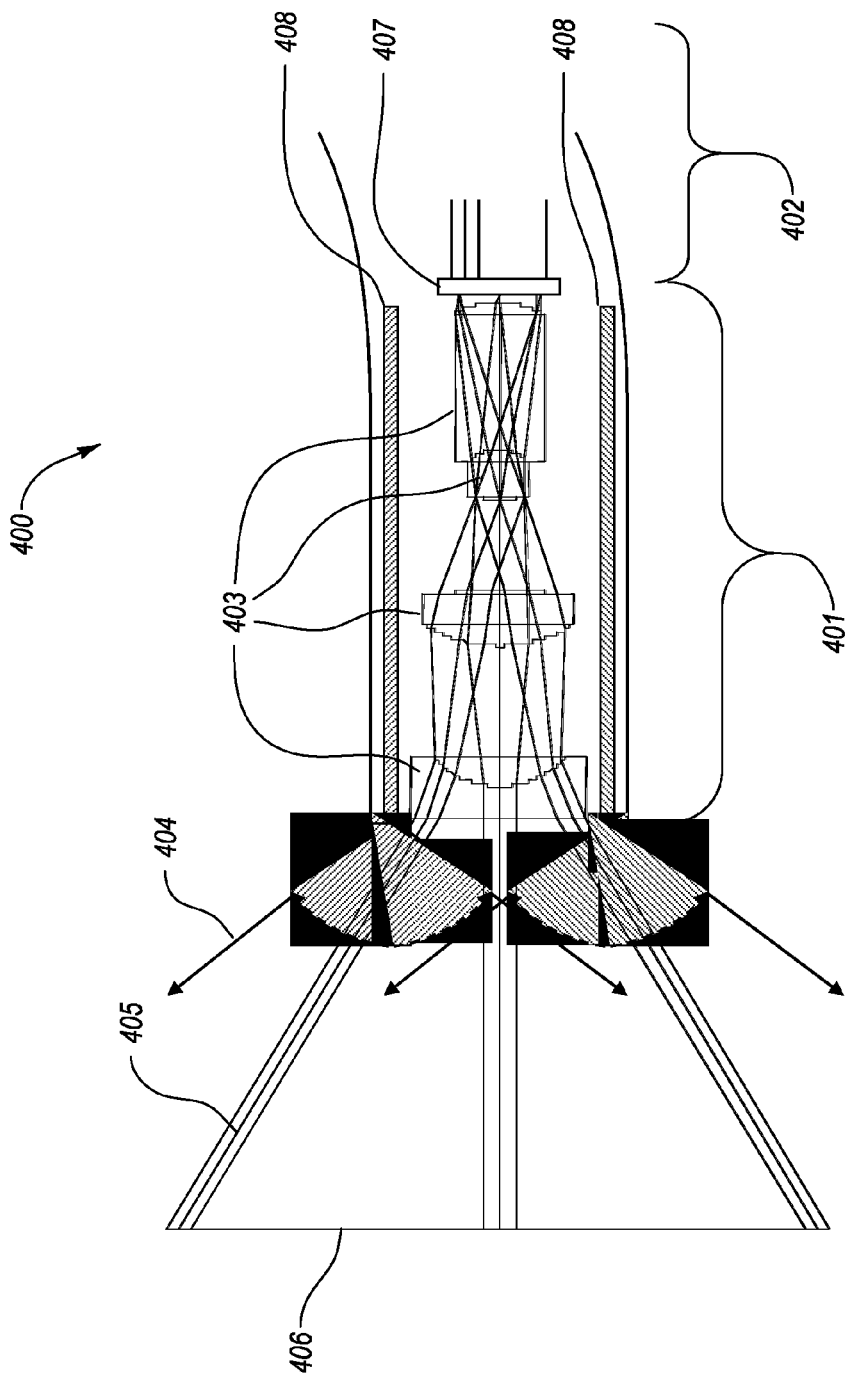
FIG. 4 illustrates the cross section of a zero degree typical flexible endoscope body (Chip on the Stick) with fiber optics illumination.

With recent technology improvements in the field of electronic imaging reducing the size of the CCD, some endoscopes used in MIS and diagnostic procedures are equipped with a high resolution distal end camera system, commonly referred to as "Chip on a Stick", one example of which is illustrated in FIG. 4. Flexible endoscopes can use a color CCD chip 407 at the distal end of the endoscope 400 directly capturing the imaging rays 405 through the objective lens assembly 401, in which case the flexible portion 402 of the endoscope body, contains only power and communication wires for the CCD camera at the distal tip, rather than imaging optics 403 which is located in the rigid portion (containing the objective lens assembly 401) of the endoscope 400. Light guides 408 can still be necessary for this type of electronic scope to provide adequate lighting 404 of the surgical site 406 for imaging purposes.

Figure 5:
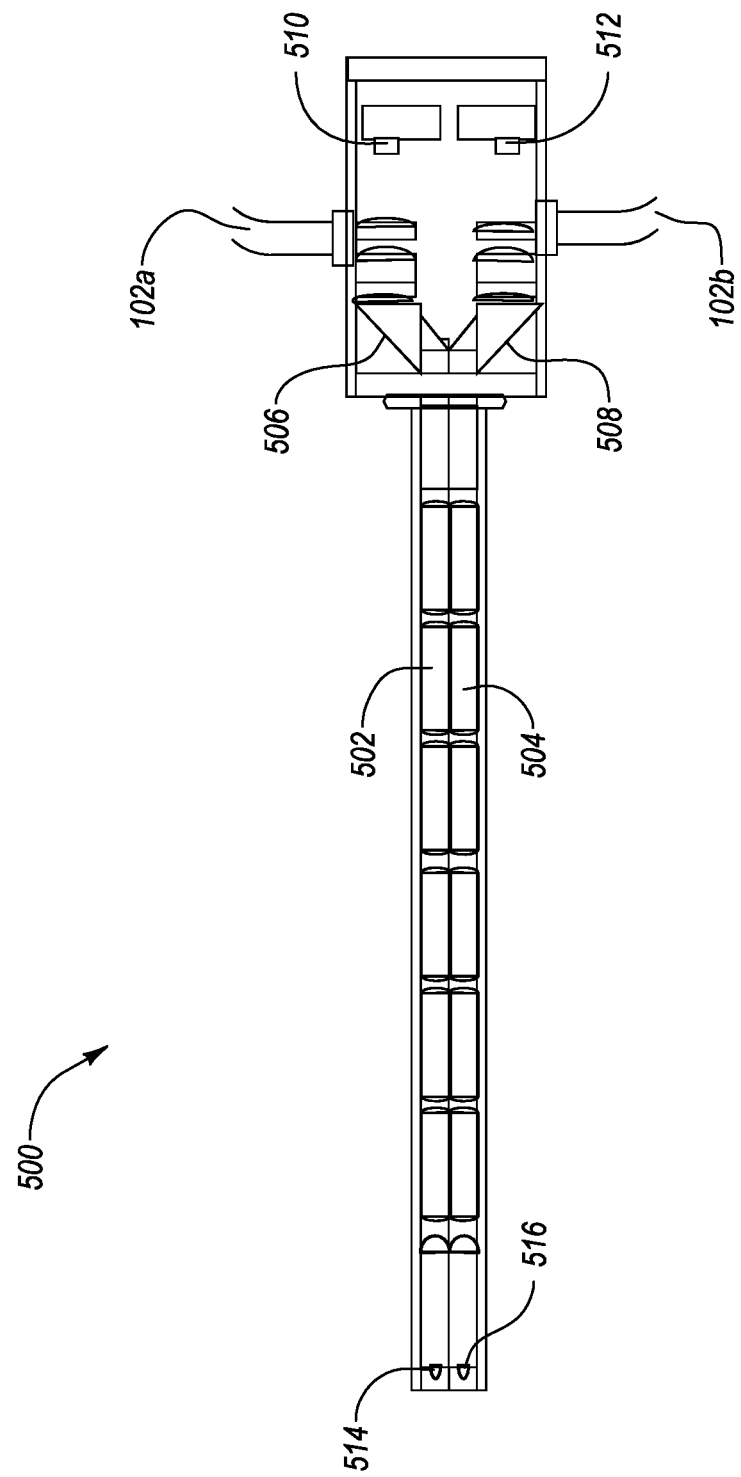
FIG. 5 illustrates a dual channel rigid stereo endoscope, with dual fiber optic illumination ports.

Other MIS systems can make use of robotic surgical tools and instruments, and/or provide stereoscopic images of the surgical site using a stereo endoscope 500 with two separate imaging channels 502 and 504, two separate camera modules 506 and 508, and two separate color image sensors 510 and 512, as depicted in FIG. 5, improving the surgeon's dexterity, precision, and speed of operation. In these more sophisticated MIS imaging applications more specific types of illumination systems or multiple illuminators 102a and 102b can be used. However having two imaging channels 502, 504 and most often dual illuminators 102a, 102b can make these stereo endoscopes bulky and the diameter of the endoscope large. Alignment of the two sets of optics in each of the imaging channels 502, 504, as well as with respect to each other, can also makes these endoscopes especially hard to manufacture and align. This can also be true with flexible stereo endoscopes such as depicted in FIG. 4.

Figure 6:
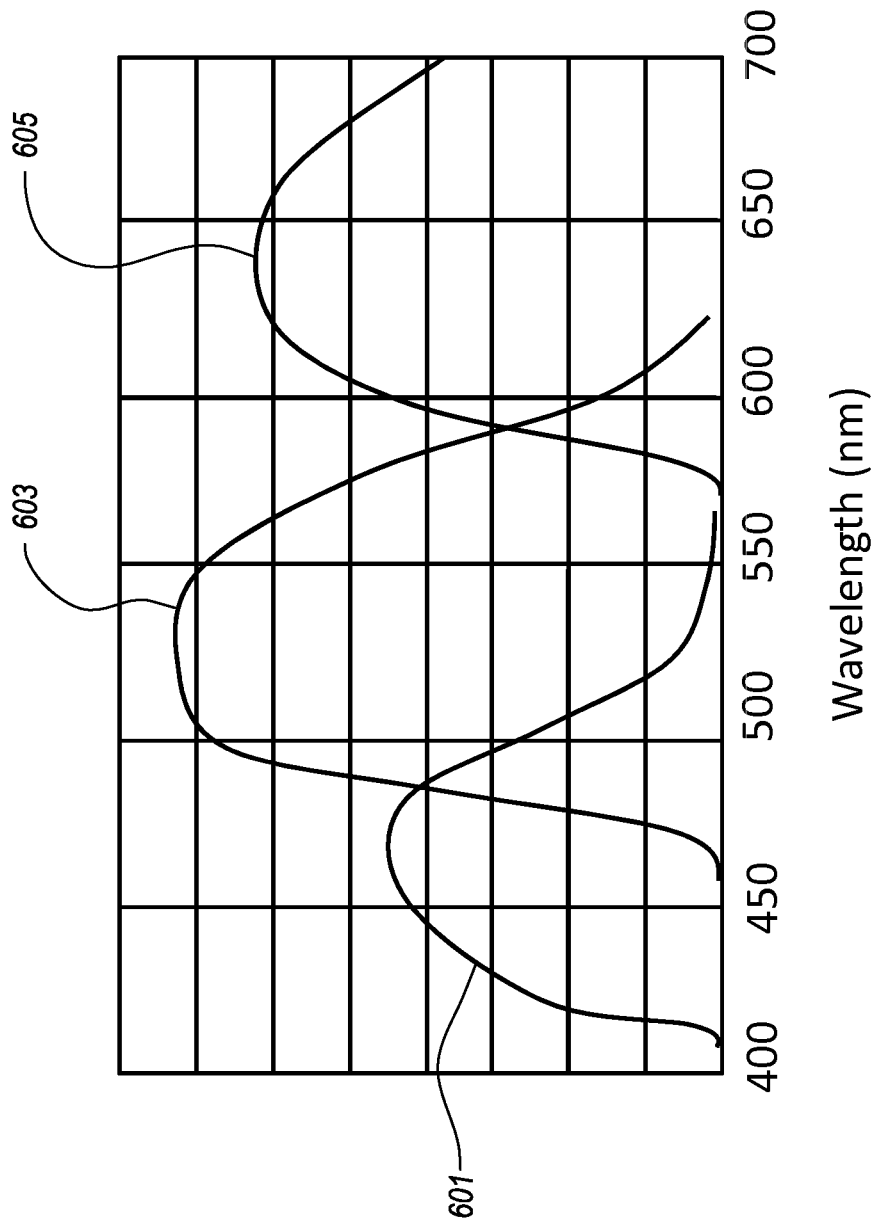
FIG. 6 illustrates RGB color filter spectrum used in a typical RGB color display or capture device.

The endoscopes can also use color CCD or CMOS cameras, which use alternate color dies on the individual pixels to capture color images. Green and red, and green and blue pixels are alternated in rows. The 3-chip CCD cameras (red CCD chip, blue CCD chip, and green CCD chip) can also be used in high resolution applications, where all the pixels in each CCD are dedicated to detecting the single color content of the image, using RGB filters in front of each camera chip. The RGB spectrum of the filters used in 3-chip CCD camera are typically matched to the RGB filter set used in an RGB color display such as depicted in FIG. 6. The individual color captured images (color components) from the 3 CCDs are then put together electronically, as the multi-color image is reproduced on the viewing display.

Figure 7A:
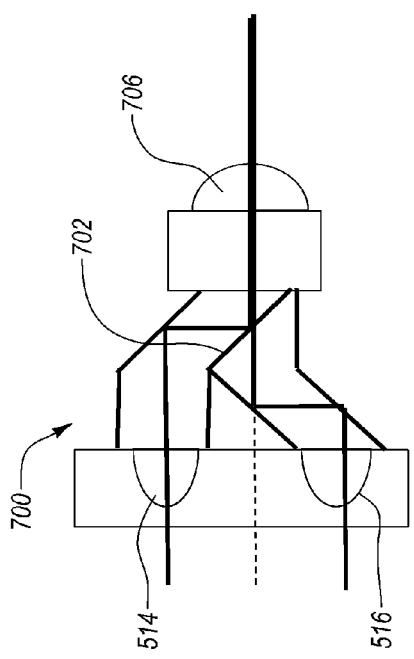
FIGS. 7a and 7b illustrate an objective lens assembly of a stereo endoscope equipped with dichroic beam splitter, wavelength multiplexing the light from the dual stereo ports into the same objective lens and single channel relay optics of an endoscope.
Figure 7B:
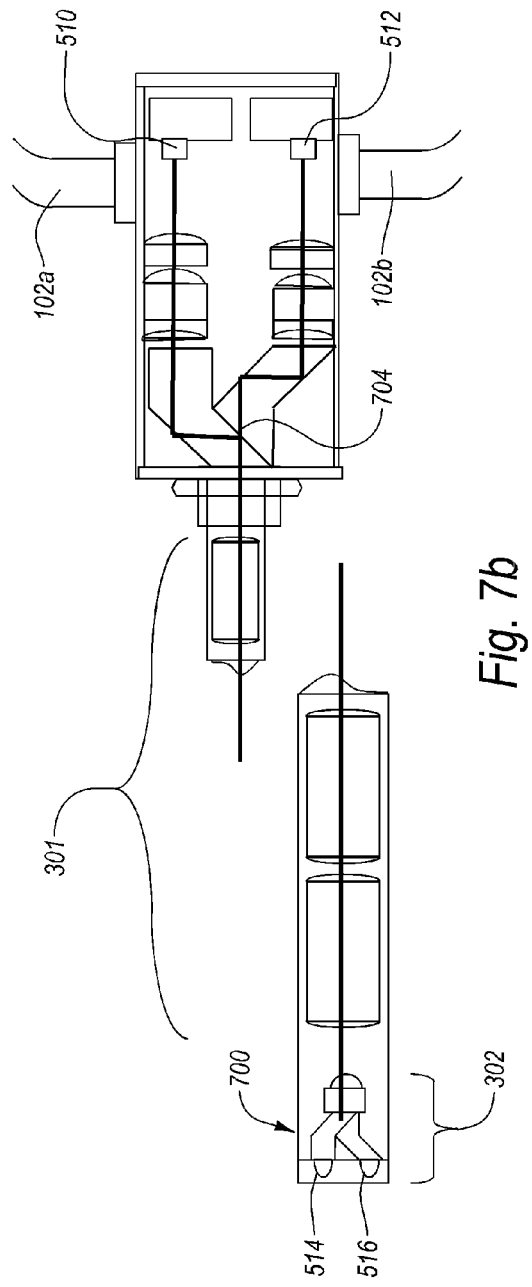

In broadband visible endoscopy, regardless of the illumination source being an outside light source or solid state illumination inside the body, it is possible to incorporate special wavelength multiplexing optics in the objective assembly of the endoscope, where various wavelengths of light are captured via different areas (ports) in the endoscope, and combined into a single endoscope channel using dielectric coated mirrors or beam splitters. In fact using a white light source as it is being used already, with appropriate dichroic coatings in the stereo objective lens assembly of a stereo endoscope, such as the endoscopes 100, 300, 400, 500 presented in FIGS. 1 and 3-5, it is possible to have a separate set of the RGB spectra go through each side of the stereo objective lens assembly 700 of FIGS. 7a-7b. FIG. 7a illustrates the stereo objective lens assembly 700, where using a dichroic beam splitter 702, both sets of RGB image information from each of the stereo ports 514 and 516, are combined to go through a single set of relay optics (see, e.g., 301, FIG. 3). These two sets of RGB images containing the stereo image information can be appropriately split back, or rejoined using a separate dichroic mirror 704 (similar to dichroic beam splitter 702) to appropriately set the stereo images on the right and left eye color sensors 510 and 512 as depicted in FIG. 7b, or be split further onto two 3-chip RGB camera modules (one 3-chip sensor for each of the stereo channels). This can effectively convert a stereo endoscope into a much smaller diameter and less complicated single channel endoscope.

Figure 8:
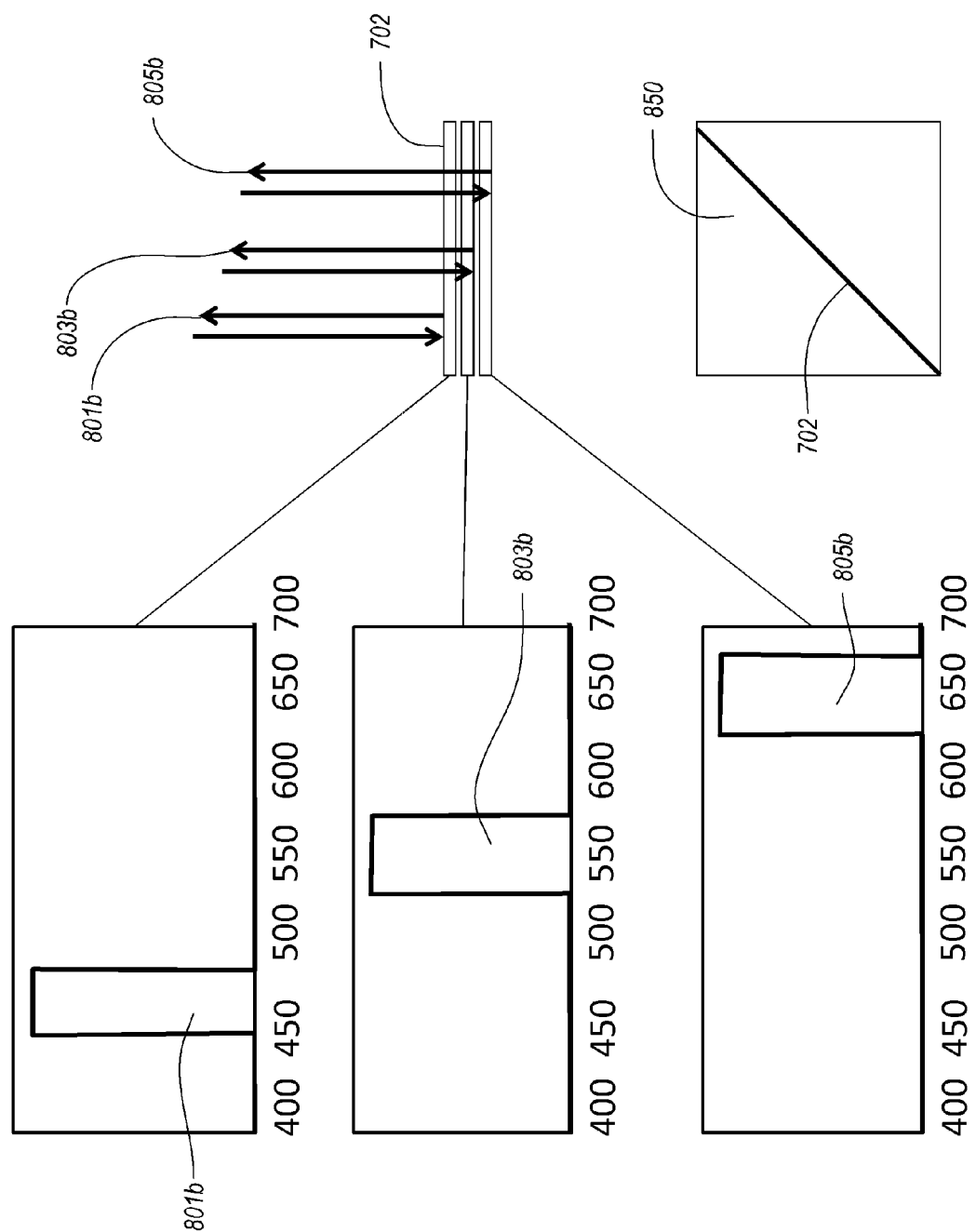
FIG. 8 illustrates the 3-band RGB dichroic mirror in beam splitting geometry that can be used in stereo objective assembly of FIGS. 7a-b.

FIG. 8 represents an example multi-wavelength dichroic beam splitter 702 (or 704) made of multiple dielectric coatings, to be used at a 45 degree incidence angle inside a cube dichroic beam splitter 850. The dichroic beam splitter 702 is designed to reflect specific wavelength ranges such as 801b in blue, 803b in green, and 805b in red, while transmitting all other wavelength. FIG. 9a represents the reflection spectra of the dichroic beam splitter 850 with wavelength ranges 801b, 803b, and 805b of a first RGB spectrum, and FIG. 9b represents the transmission spectra of the dichroic beam splitter 850 with the wavelength ranges 801a, 803a, and 805a of a second RGB spectra. Thus, in FIGS. 7a-b, the endoscope stereo port 514 can sample or image the scene in wavelength ranges 801b, 803b, and 805b that reflect from dichroic beam splitter 702, and the stereo port 516 can sample or image the scene in wavelength ranges 801a, 803a, and 805a that transmit through the dichroic beam splitter 702. Thereafter, both sets of wavelengths can pass through the same objective lens 706 and single channel relay lenses (see, e.g., 301, FIG. 3)), and together cover a portion of or the entire visible range of wavelengths in FIG. 6. As an example, the wavelength ranges 801a, 801b, 803a, 803b, 805a, and 805b could each cover roughly a 50 nm span of wavelengths in the visible wavelength range of interest (from 400 nm in blue to 700 nm wavelength in red). Namely, in one embodiment, roughly 400 nm to roughly 450 nm could represent wavelength range 801a, roughly 450 nm to roughly 500 nm could represent wavelength range 801b, roughly 500 nm to roughly 550 nm could represent wavelength range 803a, roughly 550 nm to roughly 600 nm could represent wavelength range 803b, roughly 600 nm to roughly 650 nm could represent wavelength range 805a, and roughly 650 nm to roughly 700 nm could represent wavelength range 805b (depicted in FIGS. 9a-b).

The endoscopes of the current disclosure may also include LED illumination. There are many advantages in using LEDs for this type of spectral illumination in endoscopy. LED lifetimes are more than an order of magnitude longer than bulb type light sources (50 k hours depending on the drive condition). The long lifetime in conjunction with the reliability associated with solid state lighting practically eliminates any lamp outages in an MIS procedure, where dependable illumination is one of the most critical parts of the system. In fact LED lifetime is more in line with the usage lifetime of most MIS surgical tools.

LED power consumption is also much lower than high power light sources. The LED illumination system is most efficient since there is no need for i) transferring light from the source through fiber optic light guides, ii) coupling the light into the scope light guides, or iii) transmitting through the fiber optic light guides through bends in the fiber. Light powers in the order of 1000 lumens are in fact possible with use of few high-power LEDs.

Further, LEDs are robust, and do not break, unlike fiber optic light guides. Properly-encapsulated LEDs can withstand severe environmental conditions and cleaning procedures.

LEDs do not produce any electromagnetic interference, thus eliminating the need for complicated EMI management system such as Faraday caging. Because of size, reliability and safety of LEDs, these light sources can be an ideal choice for "in location" illumination of the object inside the body. Where only electrical power is transmitted to the light source inside the body along with possible electrical control signals.

The use of LEDs can, thereby, eliminate the need of conventional fiber-optic illumination guides within an endoscope body. By eliminating conventional fiber-optic illumination guides inside the endoscope body, there is more space for the imaging optics, where the size directly relates to the image information transfer capability of the system. With more space available to the imaging optics, larger diameter optic-scan be used, making larger image FOVs and higher resolution possible. Alternatively, without the fiber-optic illumination, the diameter of the endoscope can be made smaller.

In addition, LEDs do not require a warm-up procedure. LEDs are capable of providing instant illumination with the exact color point at initiation. Optical power and color maintenance over the lifetime of the LED are also critical features of solid state light sources.

By using three color LEDs (red, green, and blue) and synchronizing a black and white camera system to grab the three time-synchronized color component images (or wavelength multiplexing), the use of color camera chips or the high resolution 3 CCD chip cameras can be eliminated. Since a single CCD camera can be used to capture the three color images in a time synchronized fashion, each color component image takes advantage of the full CCD image resolution in each frame 1002 of the video stream 1010 from a black and white sensor as shown in FIG. 10a, by incorporating all the pixels in each color image component. FIG. 10a represents the black and white video frame sequence or video stream 1010 separated into 3 sets of color video frames 1001a, 1003a, and 1005a according to a 3-color (RGB) LED turn-on sequence. FIG. 10b illustrates the missing color frames (when the particular LED color illumination was off) being filled with time interpolated video frames of that particular color, using frames from before and after the missing frames to achieve full uninterrupted video stream of RGB frames 1001b, 1003b, and 1005b.

Examples embodiments of rigid and flexible endoscopes having LED illuminators and CCD image cameras are shown in FIGS. 19 to 25. Simple black and white CCD or CMOS camera chips can also be cheaper to use, especially compared to a 3-chip CCD camera, where in effect the resolution of the synchronized black and white imaging CCD using synchronized color illumination or wavelength multiplexing provided by the LEDs is equivalent to a same pixel 3 CCD chip camera. Without the color filters in front of the single black and white camera used with color synchronized LED illumination, the sensor light detection sensitivity is also greatly improved allowing much faster frame rates to be used in capturing video images.

Using the color synchronized or wavelength multiplexed image capture device of the present disclosure also allows the use of much higher resolution image capture devices in chip on the stick cameras where space is limited at the distal tip of the endoscope for the image capture CCD, and where putting a 3-chip camera with it's associated optics and electronic connections at the distal tip is practically impossible. A variety of illumination configurations are possible using LED chips, where the uniformity, angle, and extent of the illumination are freely controlled by the positioning and design of the LED light sources.

Figure 11B:
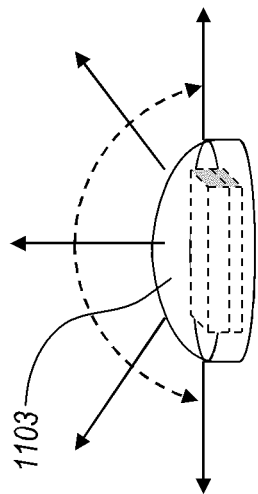
FIGS. 11a to 11d illustrate various single LED sources, without and with various encapsulation optics.
Figure 11D:
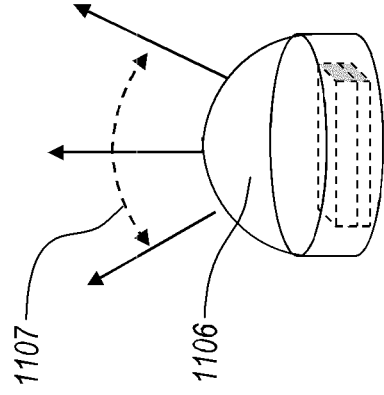
Figure 11A:
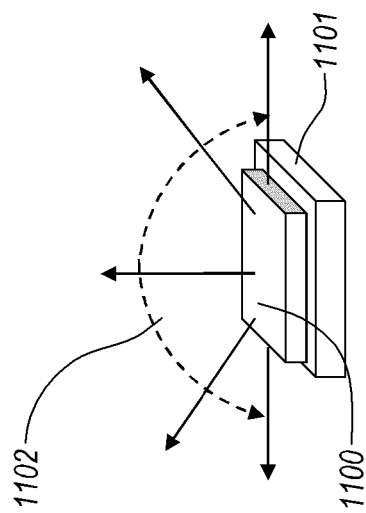

FIGS. 11a through 11d illustrate various configurations of LED output. FIG. 11a depicts a LED 1100 disposed on a base or substrate 1101. In particular, the LED 1100 can be unencapsulated resulting in a radiation pattern 1102 in the form of a Lambertian light source, where the light can be coupled into a light pipe, or used as is without any optics. This can make these solid state light sources useful for endoscopic illumination applications where wide angular field of view needs to be properly illuminated.

A simple lensing element can also be used in the form of an LED encapsulation, where, depending on the shape of the lens surface and the lens' distance from the LED surface, different angular illuminations or focusing of the light can be easily accomplished. FIG. 11b illustrates a simple lens encapsulation 1103 maintaining the same Lambertian light output as the unencapsulated LED, however with much higher light extraction from the LED chip. LEDs can be encapsulated and have their light coupled out more effectively into special guiding optics or into air, with molded optics encapsulation using high temperature hard silicone or some polymers. Alternatively special glass lens or guiding optics can be attached using silicone or other high temperature optical epoxy material on a single or multiple LEDs at the same time.

Figure 11C:
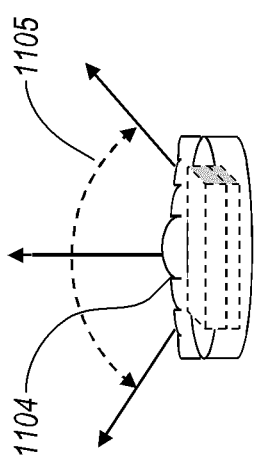

FIG. 11c depicts an additional example lens encapsulation 1104 having a surface structure including a Fresnel lens profile, diffractive optics or other refractive profiles, which can yield different angular extent of the encapsulated LED radiation pattern 1105.

FIG. 11d illustrates a simple lens 1106 encapsulation where higher index encapsulation material can be used in conjunction with positioning the lens 1106 surface farther away than the lens 1106 radius of curvature resulting in a substantial decrease in the angular extent of the radiation pattern 1107. Various dichroic color filters can also be incorporated in LED packaging geometries 11a-11d, to further define the exact color spectrum of the LED source based on color LEDs or white LEDs used.

With controllable illumination color available to 3 color LEDs, the color gamut of the illumination can be changed according to the application using the drive condition for the independent color LEDs. This can be desirable where the information content of the surgical site is mainly in a certain color, and where shifting the illumination color can increase the visibility and differentiation needed in diagnostic evaluation of the surgical scene. This adjustment can be done automatically by examination of the color content by the camera controller.

Using more illumination sources with other wavelengths than the three primary illumination colors, and matching the image detection frame capture sequence of a black and white sensor to that of the synchronized color illumination sources, can allow higher quality image capture in terms of more realistic colors. Using only primary RGB colors, the detected image color content can be within the color triangle in the CIE color diagram. Adding LEDs with other colors such as amber, cyan, and magenta, can increase the detected color gamut of the image. With the recent color displays such as flat panel LCD displays using more than just primary color illuminators (such as with 6 LED back light illuminators), it can be possible to present a "true color" image to the operator. This can be important in certain surgical applications where the color reproduction integrity plays an important role in the surgeon's perception of the scene or diagnosis of the object.

Figure 12A:
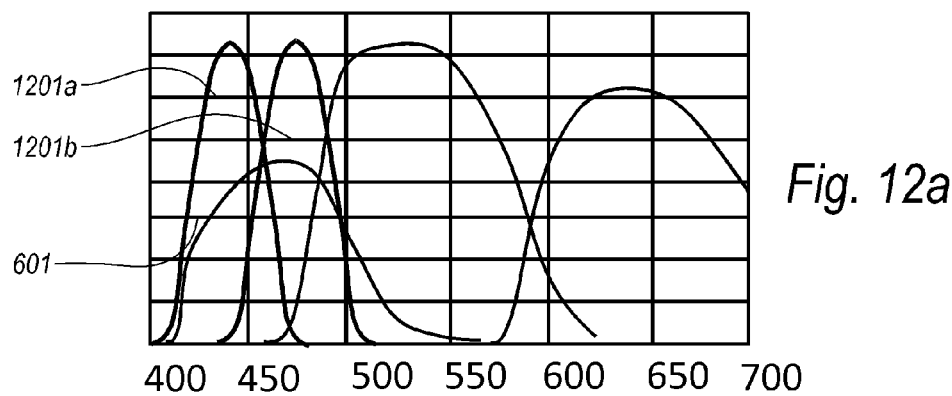
FIGS. 12a-c illustrate an illumination, where each color of the RGB imaging and display spectra, is divided into two separate illumination spectra of the source.
Figure 12B:
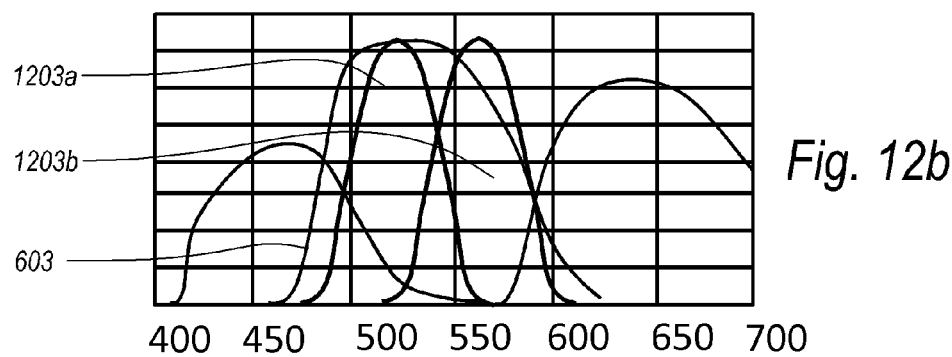
Figure 12C:
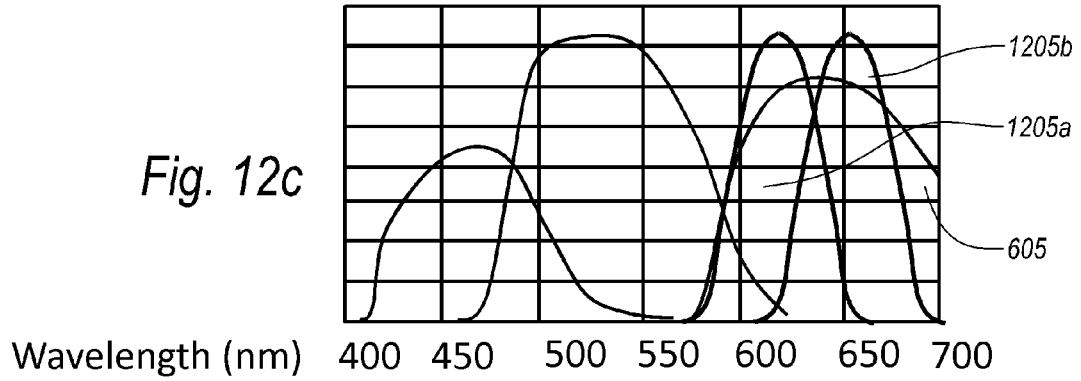
Figure 13:
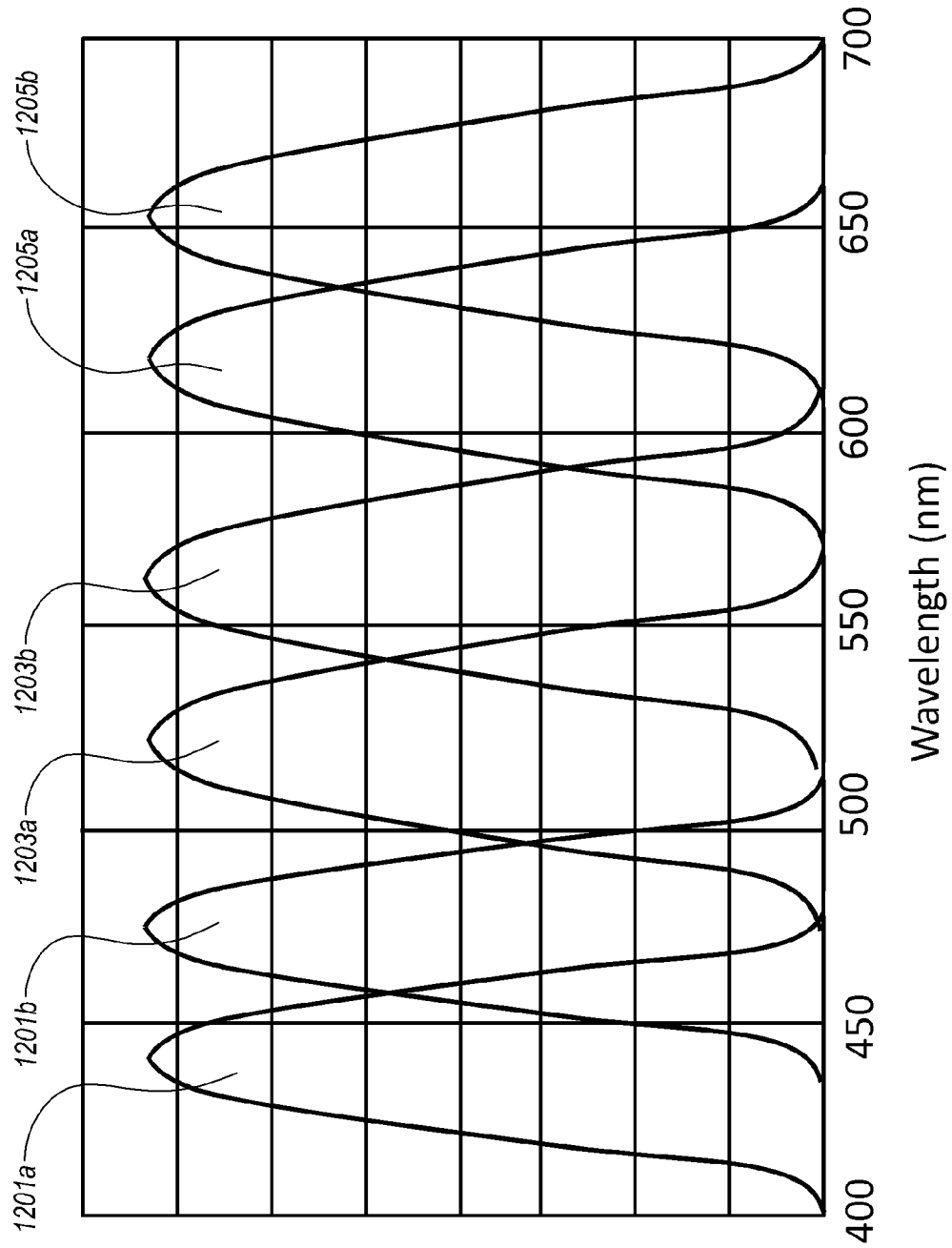
FIG. 13 illustrates illumination spectra of 6 separate sources covering the RGB imaging spectrum.

FIGS. 12a-c represent a 6 LED illumination system, where the RGB spectrum of the display presented in FIG. 6, is divided into 2 LED illuminators, each with a spectrum in each of the RGB spectra 601, 603, and 605. FIG. 12a represents the two LED spectra 1201a and 1201b in the blue spectrum 601, FIG. 12b represents the two LED spectra 1203a and 1203b in the green spectrum 603, and FIG. 12c represents the two LED spectra 1205a and 1205b in the red spectrum 605. FIG. 13 represents the overall spectrum of the 6 LED illumination of FIGS. 12a-c.

Figure 14A:
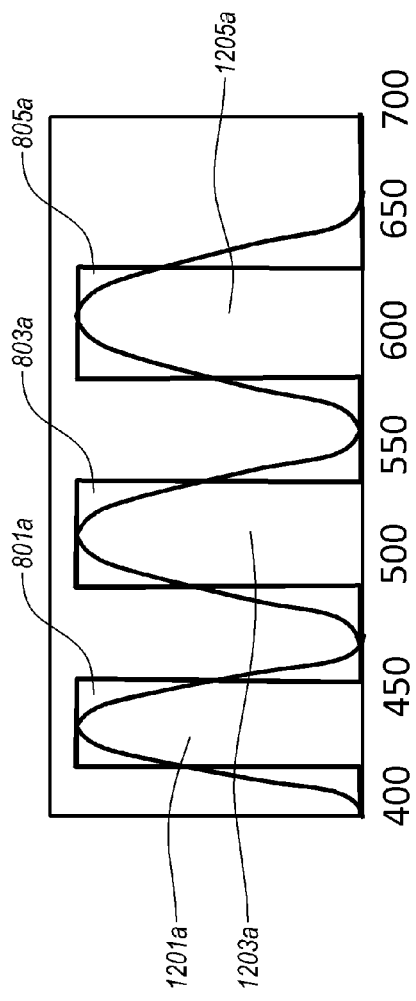
FIGS. 14a and 14b illustrate how a set of shorter wavelength RGB spectra is transmitted by the dichroic beam splitter of FIG. 8, while another set of longer wavelength RGB spectra is reflected by the dichroic beam splitter.
Figure 14B:
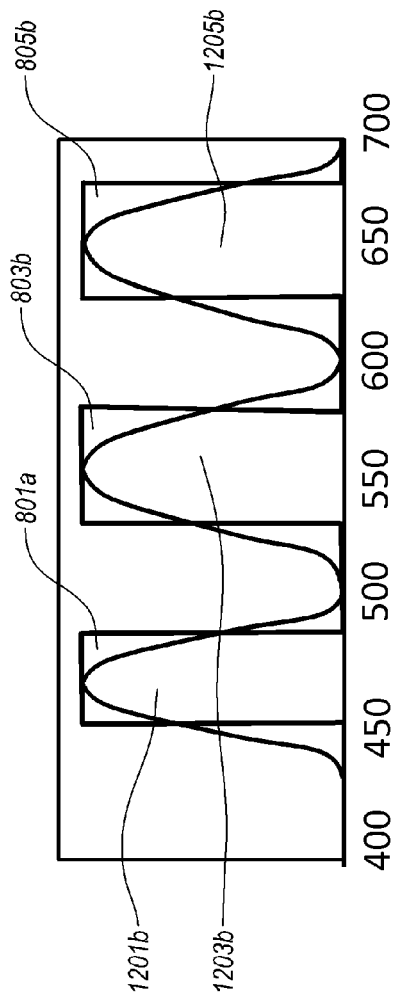

FIG. 14a depicts the LED illumination with spectra 1201a, 1203a, and 1205a transmitting through a dichroic beam filter or splitter (e.g., 702, FIGS. 7a-b), while FIG. 14b illustrates LED illumination with spectra 1201b, 1203b, and 1205b, reflecting off of the dichroic beam splitter (e.g., 702, FIGS. 7a-b). Thus, a first port (e.g., 516, FIGS. 7a-b) of such an endoscope equipped with 6 LED illuminators, could image a scene using shorter wavelength RGB spectra, as shown in FIG. 15a, and a second port (e.g., 514, FIGS. 7a-b) could image the scene using longer wavelength RGB spectra, as shown in FIG. 15b. In addition, both sets of RGB spectra can pass through the same objective lens (e.g., 706, FIGS. 7a-b) and single channel relay optics (e.g., 301, FIGS. 7a-b). Individual color LEDs or white light LEDs can also be pre-filtered using dichroic color filters similar to the ones depicted in FIG. 8, before illuminating the object or passing through the dichroic beam splitter 702 of the objective lens assembly 700 in FIG. 7.

This sampling of the scene with stereo images in different sets of RGB color, and sending both RGB color sets through a single endoscope channel, can in effect multiplex the stereo imaging data in wavelength, which can be detected using 2 or more RGB detectors, or a single detector if the two sets of RGB illuminations are interleaved in time. The 6 LED illuminators synchronized in time with a single black and white sensor frame rate, can, in a similar manner to the scheme presented in FIG. 10a-b, enable a full 3-color stereo image detection by a single sensor, with image quality of a dual 3 chip stereo endoscope camera within each stereoscopic image.

Figure 16B:
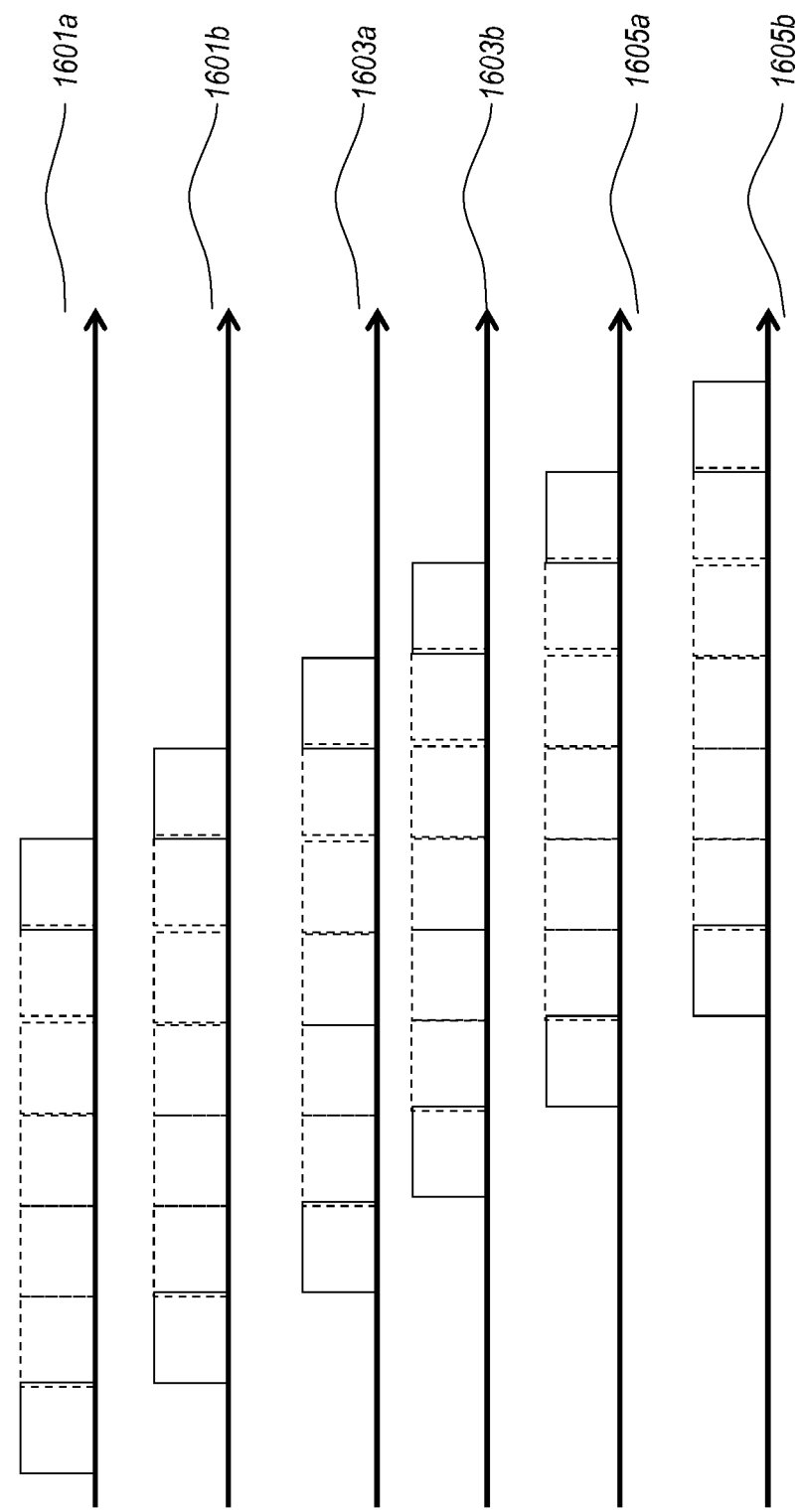
FIG. 16b illustrates time interpolation of RGB color missing frames in each of the stereo image video data, for two sets of RGB stereo images.

FIG. 16a represents demultiplexing of 6 illumination spectra frames from such RGB stereo endoscope, where the single black and white sensor video stream 1600, is split into 6 different color component video streams, where the time slot in which a specific LED is off, shows as missing frames. FIG. 16b represents time interpolation of the video data, where the missing frames are computer generated in the 6 component signals (3 RGB components for each of the stereo channels). The sequence of RGB stereo video signals can be flexible and can be interleaved so that the left and right channels can have similar RGB sampling rates in time, where 1601a and 160 1b are red frames, 1603a and 1603b are green frames, and 1605a and 1605b are blue frames of the stereo signals.

LED illumination systems can be modular, where one or multiple illumination systems can be inserted into the body independent of one another, via separate illumination bodies, at the distal end of an endoscope, or incorporated at convenient and efficient locations on surgical tool tips or cannulas.

Different solid state light sources or combination of these sources can be used to perform diagnostic as well as surgical or other functions on a body. A variety of illuminators can work in conjunction with one another and other devices to image, detect, or modify the object.

One example of an embodiment of an LED illuminated cannula 1700 according to the present disclosure used in a cannula 1700 is illustrated in FIGS. 17a and 17b. In this exemplary embodiment, the body of the cannula 1700 (or portion of it) which is clear to the light in the visible spectrum can be completely lit by white or color LEDs 1100 mounted at the proximal end 202 of the cannula 1700. Electrical power to the LEDs can be provided by a power connection 1708. As illustrated in FIG. 17b, the LED light fed into the cannula body can go through Total Internal Reflection as it travels the length of the cannula 1700 to the distal end 201, at which point the light can leave the cannula 1700 illuminating the surgical site and tools as indicated by the radiation pattern 1701. The guiding body of the cannula or output surface of the cannula, can also present other wavelength altering and tuning functions incorporated in the optical path, using various photoluminescent phosphor, dielectric coatings or optical filter die material. In FIG. 17b, a single channel stereo endoscope, such as the endoscope described in FIGS. 7a-b without the fiber optic light ports 102a and 102b can be inserted in the lighted cannula 1700.

In an additional embodiment of a cannula 1800 depicted in FIG. 18a, the cannula body can include, near its distal end 201, surface mount white or color LEDs 1100. A fixed or deployable and collapsible cone-shaped reflective cover or membrane (not shown) for these LEDs 1100 can also be inserted along with the cannula 1800 into the body, where the LED light from the body of the cannula 1800 is directed more towards the distal end 201 of the cannula 1800.

FIG. 18b illustrates another simple embodiment of a cannula 1850 with white or color LEDs 1100 mounted directly at the distal end 201 of the cannula 1850. These white or colored LEDs can also be individually or collectively color filtered to achieve specific time synchronized illumination spectrum using dichroic filters as explained in more detail above and disclosed in the corresponding figures.

As depicted in FIGS. 19a and 19b, in an example embodiment of an LED illuminated endoscope 1900, an array of white or color LEDs 1901 can be coupled removably to an extension portion 1901a extending from the distal tip of an angled endoscope tube 101. The array of LEDs 1901 can be encapsulated with lens encapsulations 1902 to establish the desired illumination field 1904 and corresponding uniformity of illuminations. FIG. 19a illustrates this example embodiment of endoscope 1900 in the side view, and FIG. 19b is and end view illustration of such embodiment. The endoscope can also include a clear imaging port 1903, and the LEDs 1901 can be encapsulated using a Fresnel type lens encapsulation 1902. Other tool insertion ports, multiple imaging objective assemblies, such as in FIG. 12a with a single port for stereo imaging, or imaging objectives with various Field of View (FOV), can be used in the clear area of the distal end of the endoscope 1900. Other solid state light sources such as laser diodes or various wavelength LEDs can be mounted in the vicinity of the LEDs 1901 depicted in this embodiment to perform other functions using the same device. Other forms of optics or optical elements such as lenses, polarizers, waveplates, and dichroic color filters can also be used in front of the LEDs 1901 or imaging ports 1903 to modify the illumination extent or for proper detection of the light.

In another embodiment of a solid state illumination within an endoscope 2000, FIG. 20a illustrates the incorporation of white or color LEDs or lasers, IR or UV solid state light sources 2001 behind the first negative lens window 2002 of the objective lens assembly. This portion of the objective lens, in effect, acts as a window for the light source 2001, since the concave portion of the first negative lens window 2002 of the objective lens assembly, is typically much smaller than the distal window of the endoscope 2000. Solid state illumination sources in this configuration can be directly mounted to this glass window around the concave area of the lens. As the illumination light leaves the glass at the distal end, the angular radiation pattern 2003 of the light expands as illumination is emitted outside the glass. Refractive polarization, waveplates, or dichroic color filters can also be implemented in the area of the negative lens window 2002 beyond the concave portion to modify the illumination characteristic. FIGS. 20b and 20c represent front and side views of such an implementation in a wavelength multiplexed stereo endoscope 2050 format, where rows of various color LEDs 2004 are used in either side of the dual negative lens ports 514 and 516, behind the window 2002. Various spectra LEDs in visible, IR or UV can be time synchronized with a single black and white sensor 2006 to obtain full spectral imaging.

In yet another example embodiment of LED illumination within an endoscope 2100, white or a combination of RGB LEDs can be used within the objective lens. As illustrated in FIG. 21a, LEDs 1103 can be mounted so that the illumination crosses the endoscope axis where the illumination light from the LEDs 1103 is combined into the imaging path using beam splitter optics 2102. FIG. 21b illustrates such beam combining optics with multiple white or RGB LEDs 1103 for the stereo objective assembly of FIG. 7a, where the light from LEDs 1103a and 1103b, for opposite stereo ports 516 and 514, are combined using complementary dichroic beam splitters 702a and 702b. Dichroic beam splitter 702a transmits an RGB set from LEDs 1103a, and reflects the complementary RGB set from LEDs 1103b for imaging through stereo port 514. Dichroic beam splitter 702b on the other hand, transmits the complementary RGB set from LEDs 1103b, and reflects the RGB set of 1103a for imaging through stereo port 516. The RGB sets once received back by the endoscope 2150 for imaging, are then combined in the beam splitter 702 where RGB set 1103b received from port 514 is reflected, and RGB set 1103a received through port 516, is transmitted (as described above and disclosed in FIG. 7a).

LEDs provide a desirable cost advantage over conventional lamp and fiber guide systems, as it replaces the expensive light sources, long fiber optic light guides to transfer light from the light source to the scope, and the illumination light guides inside the scope as well. Low level power is only needed for the LED light sources, thus the electrical connection of the LEDs is much easier, and with use of low cost endoscopes one can make the whole endoscope a disposable unit.

Only electrical power and LED control signals need to be provided for the endoscope, eliminating the heavy and bulky fiber optics illumination cable connection to the scope, increasing the maneuverability of the endoscope. FIG. 22 illustrates a single channel endoscope 2200 equipped with dual RGB LED powered stereo objective assembly 2150 of FIG. 21, where both stereo images are combined, passed through single relay optics, and detected using a single sensor 2206 in a 6 cycle (2× RGB) time synchronized fashion, such as described above and disclosed in the corresponding figures. The single sensor endoscope camera unit 2201 can power the LEDs using a disposable or rechargeable battery 2204 turning them on one at a time, and connect to the external control and display unit 2250 wirelessly using a transmitter and receive unit via a wireless connection 2208 inside the camera unit 2200. This makes the endoscope 2200 completely connection free and very easily maneuverable.

Wireless connection 2208 can transmit the single video stream (e.g., 1600, FIG. 16*a*), from the single black and white sensor 2206 that captures the full RGB stereo video signal from both stereo ports 514, 516, to the control and display unit 2250 of FIG. 22. This saves the transmission bandwidth otherwise necessary to transmit 2 sets of 3-chip RGB camera video information, by ⅙. The demultiplexing of the single 6 wavelength video information and processing represented in FIGS. 16*a* and 16*b*, similar to one described in FIG. 10 for a single RGB signal, can all be done inside the control/display unit 2250, where the processed RGB image videos of the two endoscope ports 514 and 516, can be sent to the stereo viewing ports 514*a* and 516*a*, and viewed by observer's right and left eye (514*b* and 516*b*). The 3D viewer can display the right and left RGB images on individual left and right displays, or on a single time synchronized display, where left and right video image frames are alternated and time synchronized with LCD shutters in the right and left stereo viewing ports 514*a* and 516*a*. Wireless connection 2208 can also be used to identify the endoscope 2200, illumination and imaging synchronization state, and timing signal, to the control and display unit 2250, or receive instruction and timing signal to control the illumination and imaging data from the control and display unit 2250.

Since any heat generated from the LEDs is not in the form of radiative heat, as in the case of lamps, it can be easily conducted out of the endoscope 2200, or instrument tip using a conductive layer or the endoscope 2200 or instrument body itself. Some of this heat can in fact be conducted towards the endoscope optical window, such as in the embodiment of FIGS. 20*a-c* which show endoscopes 2000 and 2050, where the LEDs 2001 and 2004 are at intimate contact with the endoscope window 2002 and its holder, which provides the proper temperature setting to avoid any condensation on the optical window during operation and additionally warms the end of the cold endoscope 2000, 2050 when it is inserted into the warm and humid body cavity. In turn a separate low power infrared LED, or a passive resistor can also be used for the purpose of heating the endoscope tip.

The side and front view of another embodiment of stereo flexible endoscope 400, is represented in FIGS. 23*a* and 23*b*, where a single color sensor 2302 is used as the stereo image capture device. The negative lens window 2002 in this case is also made into an oval shape, accommodating the two sets of RGB LEDs 2304 and 2306 mounted in a fixed position, or as two deployable LED source bodies that can flip open to a deployed position outside the scope frame in either side of the imaging optics, once the scope is inserted into the body. The RGB LED set 2304 is a short wavelength set such as represented in FIG. 15*a* (as 1201*a*, 1203*a*, and 1205*a*), and the RGB LED set 2306 is a longer wavelength set of RGB colors similar to the one represented in FIG. 15*b* (as 1201*b*, 1203*b*, and 1205*b*). Alternatively both sets of LEDs 2304 and 2306 are broadband white LEDs, with complimentary dichroic filters in front of them, with transmission characteristics similar to short and long wavelength RGB spectra depicted in FIGS. 9*a* and 9*b*. The color sensor 2302 is sensitive to detecting either RGB color set 2304 or 2306, and has spectral sensitivity similar to the display RGB spectrum of FIG. 6 or FIG. 15 (represented as 601, 603, and 605). The two RGB LED sets 2304 and 2306 can be turned on and off one at a time, synchronized with the frame rate of the RGB sensor 2302. Then, in a two-cycle fashion, the single color sensor 2302 can capture the RGB stereo images from either stereo ports 514 and 516, one at a time in an alternating manner.

In the flexible scope geometries presented in FIGS. 20*a-c*, 21*a-b*, and 23*a-b* the illumination and the mono or stereo imaging system can be incorporated at the distal tip 401 of a flexible hollow body 402 of an endoscope, where a separate articulating body can be inserted into the flexible hollow body 402. In this manner the separate articulating or robotic body can be removed and reused with various illumination or imaging type flexible endoscopes that can fit over the articulating body. The articulating body can make electrical contact with the illumination and imaging tip of the endoscope as it is inserted into the flexible hollow body 402, or the flexible hollow body 402 of the endoscope can have its own battery power and electrical connection at the proximal end, with power and image data transmission lines routed along its length.

Other angled stereo scope tip geometries are also possible to implement using various mirrors and prisms in the wavelength multiplexing objective assembly, where by placing the dual input ports 514 and 516 at an angle, the distance between the two ports, which defines the stereo separation in stereo viewing, can be improved. FIGS. 24*a-c* represent various examples of such objective lens assemblies 2400*a-c*, where dichroic beam splitter 702 is used to combine the split wavelength beam from the dual ports 514 and 516, and various mirrors 2402 are used to keep the path length of each channel the same in the objective assembly as they are input with the same optical path length into the single objective lens 706. FIGS. 24*a-c* represent 90, 70, and 30 degree angled scope geometries given as possible examples, where the area between the two negative lenses is used as a mirror surface 2402 in FIG. 24*b*, and a single mirror 2402 reflecting both beams in FIG. 24*c*.

Figure 25:
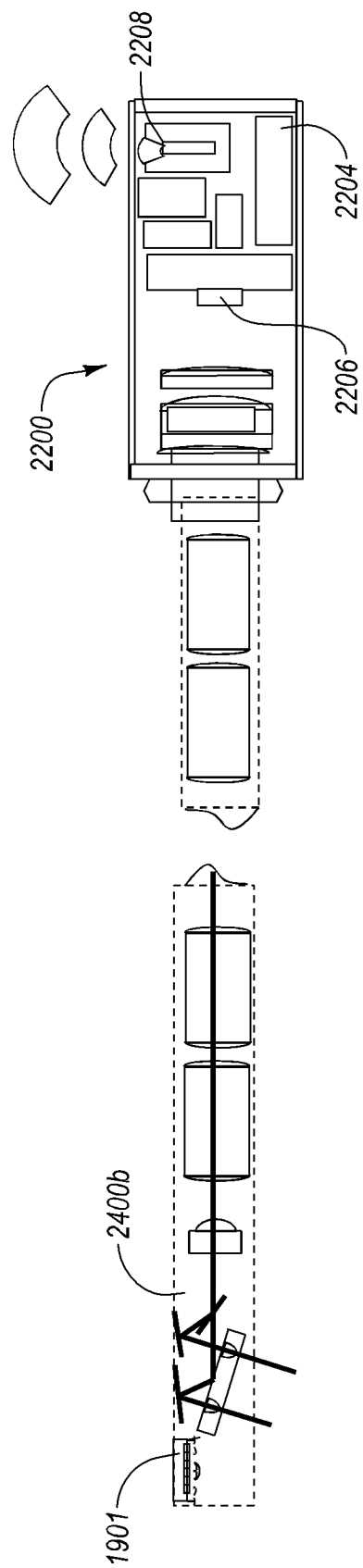
FIG. 25 illustrates the angled stereo endoscope objective assembly in an endoscope with LED illumination at the distal tip.

FIG. 25 illustrates the 70 degree angled scope objective assembly of FIG. 24*b*, used in a wireless stereo endoscope 2200 of FIG. 22, where the extended angled endoscope tip houses an array of illuminators 1901, such as depicted in FIG. 19*a*.

Figure 26:
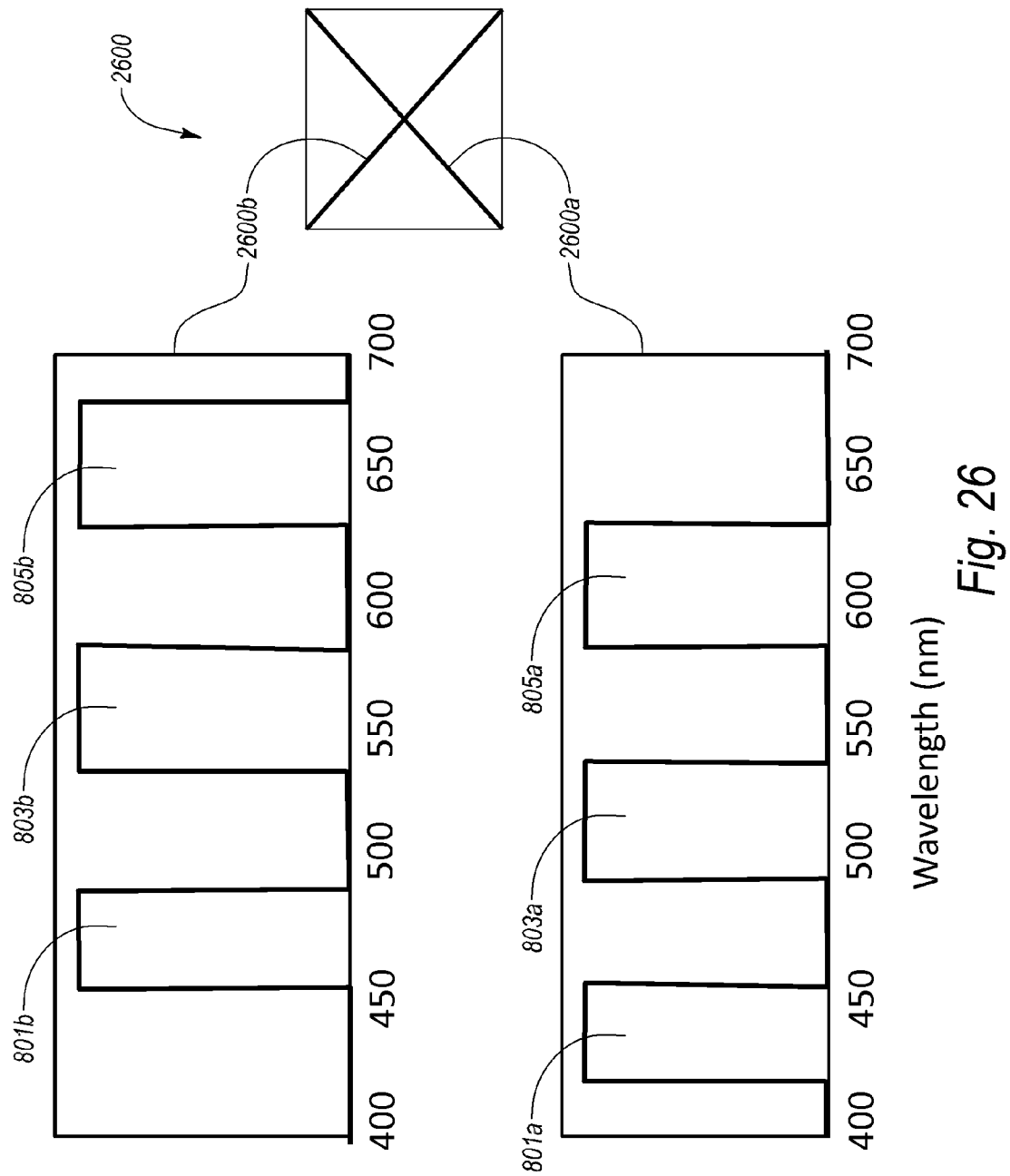
FIG. 26 illustrates a double multi-wavelength dichroic mirrors in a cube beam splitter geometry.

FIG. 26 represents a dual multi-spectra dichroic cube beam splitter 2600, made of two complementary dichroic mirrors 2600*a* and 2600*b* similar to dichroic mirror 702 described above and disclosed in the corresponding figures. Dichroic mirror 2600*b* has similar spectral reflectance to dichroic mirror 702 (801*b*, 803*b*, 805*b*), but dichroic mirror 2600*a* has complementary spectral reflectance, or similar to the dichroic mirror 702's transmission spectra, depicted in FIG. 9*b* (801*a*, 803*a*, and 805*a*).

Figure 27:
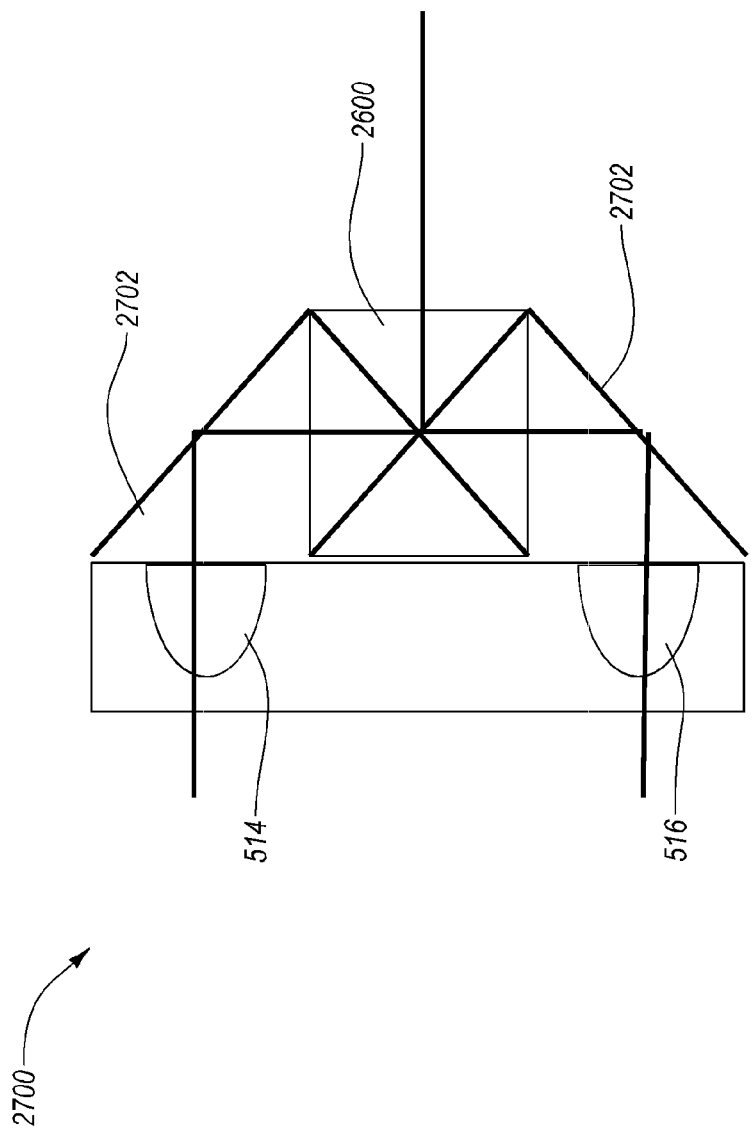
FIG. 27 illustrates a stereo endoscope objective system that multiplexes two stereo channels into a single optical channel, using the double multi-wavelength dichroic beam splitting cube in FIG. 26.

FIG. 27 represents a symmetrical dual channel, wavelength multiplexing geometry that can be used as a stereo objective assembly 2700 similar to the assembly 700, in a single port and/or a single sensor endoscope. Reflective 45-degree angle prisms 2702 can direct the light from the dual ports 514 and 516 to the beam combining dual dichroic prism 2600, where the light from both channels can enter the single objective lens, relay optics or imaging optics of an endoscope. Such dual channel wavelength multiplexing geometry can alternatively be used in any of the stereo endoscopes described above, and also be extended to a quad geometry where 4 wavelength multiplexing dichroic mirrors are used in a cube to combine 4 wavelength channels of choice in a spectral imaging objective lens that could work in IR, UV, or any range of visible spectra.

In addition to the above example embodiments 1900, 2000 and 2100, where the LED illuminators are used in fixed positions within the endoscope body, other deployable embodiments are possible for effective illumination of the surgical site. In these deployable embodiments, the LED illuminators can be deployable from an insertion position in which they are held within the insertion body or within a close profile of the insertion body, to an operational position where they are conveniently pointed to the object of interest. In operational position, the illumination light can be directed to the surgical site from beyond the endoscope body, where deployment of the LED holder structure positions the illuminators off axis from the imaging axis, possibly increasing the collection efficiency of the imaging optics.

Figure 28A:
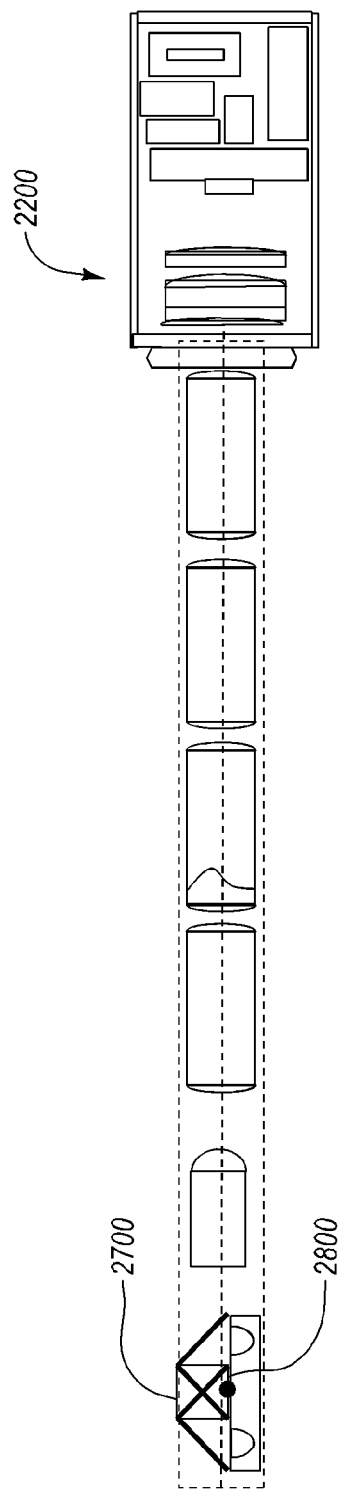
FIGS. 28a and 28b illustrate a deployable wavelength multiplexed stereo objective in insertion position and in use position after the deployment inside the body, on a rigid endoscope.
Figure 28B:
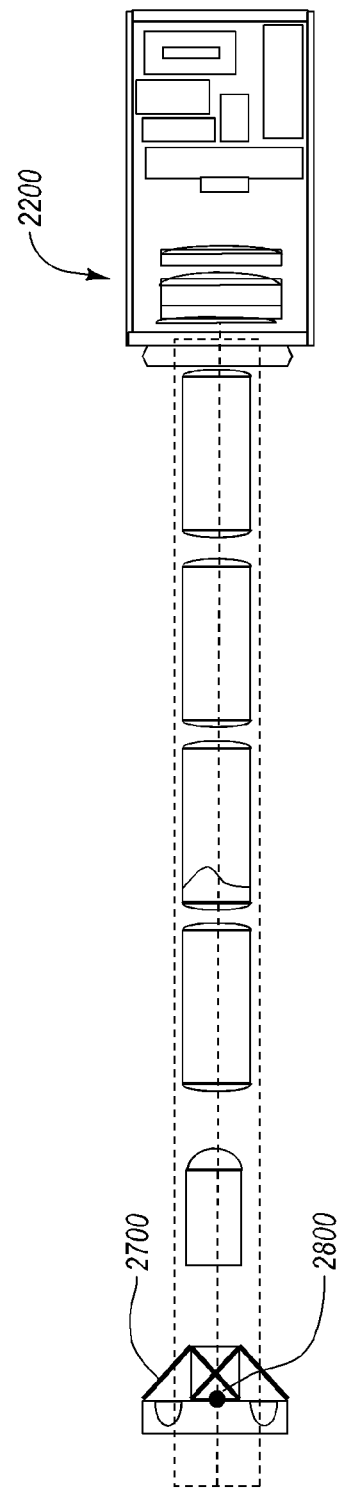

The dual channel wavelength multiplexing geometry 2700 can also be used as a movable or deployable body, at the distal tip of an endoscope 2200 with or without LED illuminators. FIGS. 28a-b and FIGS. 29a-b represent the stereo objective assembly 2700 as a movable body, which is positioned within the frame of the endoscope 2200 while entering into the body. When the endoscope 2200 is positioned inside the body, the 2700 assembly can be pivoted into place around the axis 2800, where the light received from its stereo channels can properly enter the fixed optics and sensors within the endoscope 2200. FIGS. 28a-b show the use of such deployable tip in a rigid endoscope format, while FIGS. 29a-b show the implementation of such deployable stereo objective in a flexible endoscope format 400. In this and similar embodiments, the deployable geometry optical assembly 2700 and its stereo separation can be made larger than otherwise feasible within the frame of the endoscope.

In alternate embodiments of all of the endoscopes, cannulas and other devices described above that use LEDs for illumination, Solid State Laser Diodes (LD) can also be used at the distal end of tools, insertion tubes, catheters, multi-port imaging scopes, cannulas, etc. where LDs of various wavelengths can be multiplexed using dielectric coatings to take various or same routes through the endoscope. Blue or UV Laser diodes or LEDs can be used to actively induce bioflorescence in the live tissue under observation, enabling florescence imaging at specific bio-florescent detection wavelengths determined by the wavelength multiplexing filter(s) in the imaging objective of the endoscopes as described earlier. Infrared Imaging could use IR solid state light sources to illuminate intra-vein or close tissue diagnostic and surgical procedures. IR detectors and cameras can be used for thorough tissue and blood imaging along with external infrared light sources that have appreciable penetration depth in human tissue, blood or other bodily fluids such as urine. Using a high intensity IR source at the surgical or examination site with control over the intensity, radiation pattern, and the direction of illumination can help with the most critical surgical procedures inside the vein, heart, and other body organs. Infrared wavelength imaging can also be multiplexed in with the visible wavelength stereo imaging sequence, as alternating IR image detection frames, using dichroic beam splitters/filters such as described above that have transmission or reflection characteristics in the IR wavelength range.

Miniature, optical components such as lenses, mirrors, beam splitters, polarizers, waveplates, etc. can also be used in conjunction with solid state light sources (laser diodes and LEDs), within the multi-port objective assembly to further manipulate the illumination characteristics of the light and extend the functionality of wavelength multiplexing optics. Lenses for example, can be used to direct the light to larger or smaller areas of the scene, or focusing the beam to a small area on the object depending on the application, or to further collimate the light in the imaging path going through the wavelength multiplexing optics.

Polarization characteristics of the solid state laser or polarized LED light output can also be used in special detection schemes, enhancing the wavelength multiplexing mechanism, or where depth perception or other biological imaging characteristics that depend on the polarization of the light can be better perceived, similar to polarized microscopy.

The examples disclosed herein may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A device for insertion into a body cavity, the device comprising:
    a tubular portion having a proximal end and a distal end, the distal end being configured to be at least partially inserted into the body cavity;
    an objective lens assembly positioned in the rigid section of the tubular portion;
    an image capture device positioned to capture imaging rays through the objective lens assembly in the rigid section of the tubular portion;
    an optical assembly configured to collect spectral imaging data from an area inside the body, wherein the optical assembly is configured to incorporate at least two separate wavelength dependent images with separate light spectra;
    one or more light sources configured to illuminate the area inside the body and positioned on an internal sidewall of the rigid section such that light from the one or more light sources is directed radially inward;
    a beam splitter configured to combine the illumination from first and second light emitting devices of the one or more light sources into a path of imaging rays; and
    optics comprising first and second dichroic beam splitters, the first dichroic beam splitter configured to transmit a first red/green/blue set from the first light emitting devices and to reflect a second, complementary red/green/blue set from the second light emitting devices through a first stereo port, and the second dichroic beam splitter configured to transmit the second, complementary red/green/blue set from the second light emitting devices and to reflect the first red/green/blue set through a second stereo port separate from the first stereo port.

2. The device of claim 1, wherein the one or more light sources are configured to produce at least two wavelength dependent images with separate light spectra that travel different routes through at least a portion of the device.

3. The device of claim 1, wherein at least two portions of the spectral imaging data, each having a separate light spectra, are time synchronized with a frame rate of at least one image sensor.

4. The device of claim 3, wherein time synchronized spectral imaging data is made to travel from different parts of the device at the same time or different times.

5. The device of claim 3, wherein time synchronized spectral imaging data is combined into the same optical path in the device.

6. The device of claim 3, wherein time synchronized spectral imaging data are collected by one or more black and white, single color, or multi-colored image sensors.

7. The device of claim 1, wherein the first and second light emitting devices are positioned on opposing sides of the tubular portion such that illumination from the light emitting devices crosses a longitudinal axis of the tubular portion.

8. The device of claim 1, wherein the at least two separate wavelength dependent images are combined, passed through single relay optics, and detected using a single sensor in a time synchronized fashion.

9. A device for insertion into a body cavity, the device comprising:
- a tubular portion having a proximal end and a distal end, the distal end being configured to be at least partially inserted into the body cavity;
- at least one solid state electro-optic element disposed in the tubular portion and comprising first and second light emitting devices and a dichroic beam splitter configured to combine first and second red/green/blue spectra from the first and second light emitting devices to form a path of imaging rays, the dichroic beam splitter comprising:
- first and second beam splitters, the first beam splitter configured to transmit the first red/green/blue spectra from the first light emitting devices and to reflect a second, complementary red/green/blue spectra from the second light emitting devices through a first stereo port, and the second beam splitter configured to transmit the second, complementary red/green/blue spectra from the second light emitting devices and to reflect the first red/green/blue spectra from the first light emitting devices through a second stereo port separate from the first stereo port;
- at least one image sensor configured to receive the path of imaging rays; and
- a power source electrically coupled to the at least one solid state electro-optic element and the at least one image sensor.

10. The device of claim 9, further comprising at least one of detecting elements, imaging elements, wavelength manipulating elements, and combinations thereof, disposed in the tubular portion.

11. The device of claim 10, further comprising a plurality of solid state electro-optic elements of various wavelengths, wherein the plurality of solid state electro-optic elements are electrically linked to an image capture device disposed in the tubular portion, and wherein the plurality of solid state electro-optic elements are time synchronized with the image capture device to provide a color image.

12. The device of claim 11, wherein a driving scheme of the solid state electro-optic elements and data from the image capture device is transmitted wirelessly to a control and display unit in raw or processed format, while information on how to run the light emitting devices and detection is obtained wirelessly from the control and display unit.

13. The device of claim 10, wherein the at least one solid state electro-optic element is part of a combination illuminator and imaging system, wherein the combination illuminator and imaging system is electrically coupled to the tubular portion to supply electrical power to the at least one solid state electro-optic element.

14. The device of claim 10, wherein the at least one solid state electro-optic element is disposed in relation to the tubular portion such that light emitted from the at least one solid state electro-optic element passes through at least a portion of the at least one of detecting, imaging, and wavelength manipulating elements.

15. The device of claim 10, further comprising an imaging window disposed in the distal end of the tubular portion, wherein the at least one solid state electro-optic element includes a light source, and wherein conductive heat generated from the at least one solid state electro-optic element is coupled to the imaging window to prevent condensation on the imaging window.

16. The device of claim 10, wherein the at least one solid state electro-optic element, detecting elements, imaging elements, and/or wavelength manipulating elements are deployably configured such that in an insertion position, the at least one solid state electro-optic element is contained within the tubular portion, and in a deployed position, the at least one solid state electro-optic element is disposed exterior of the tubular portion such that optical images are able to pass through the detecting elements, imaging elements, and/or wavelength manipulating elements.

17. The device of claim 9, wherein the power source comprises a disposable or rechargeable battery.

18. The device of claim 9, wherein the at least one solid state electro-optic element is positioned in a rigid portion at the distal end of the tubular portion and remaining portions of the tubular portion are flexible.

19. The device of claim 9, wherein the first and second light emitting devices comprise sets of light emitting devices.

20. The device of claim 9, wherein the one or more light sources comprises one or more sets of light emitting devices.

* * * * *